(12) United States Patent
Galasso et al.

(10) Patent No.: US 12,154,448 B2
(45) Date of Patent: *Nov. 26, 2024

(54) INCORPORATING REAL WORLD PHYSICAL ACTIVITY INTO A VIRTUAL WORLD ENVIRONMENT

(71) Applicant: Fox Factory, Inc., Duluth, GA (US)

(72) Inventors: Mario Galasso, Sandy Hook, CT (US); Wesley E. Allinger, Santa Cruz, CA (US); David M. Haugen, Pacific Grove, CA (US); Robert David Kaswen, Watsonville, CA (US); Mark Stephen Fitzsimmons, Gilroy, CA (US)

(73) Assignee: Fox Factory, Inc., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/371,919

(22) Filed: Sep. 22, 2023

(65) Prior Publication Data

US 2024/0127711 A1    Apr. 18, 2024

Related U.S. Application Data

(63) Continuation of application No. 16/869,601, filed on May 8, 2020, now Pat. No. 11,769,423.

(60) Provisional application No. 62/845,211, filed on May 8, 2019.

(51) Int. Cl.
| | |
|---|---|
| *G09B 19/00* | (2006.01) |
| *A63B 71/06* | (2006.01) |
| *G06Q 30/0207* | (2023.01) |
| *G06Q 30/0601* | (2023.01) |

(Continued)

(52) U.S. Cl.
CPC ...... *G09B 19/0038* (2013.01); *A63B 71/0622* (2013.01); *G06Q 30/0209* (2013.01); *G06Q 30/0631* (2013.01); *A63B 2071/0694* (2013.01); *A63B 2230/06* (2013.01); *G09B 9/00* (2013.01); *G16H 40/67* (2018.01)

(58) Field of Classification Search
CPC .... G09B 19/0038; G09B 9/00; G09B 29/007; A63B 71/0622; A63B 2071/0694; A63B 2230/06; G06Q 30/0209; G06Q 30/0631; G16H 40/67; G16H 20/30; G16H 50/30
See application file for complete search history.

(56) References Cited

U.S. PATENT DOCUMENTS

| | | | | |
|---|---|---|---|---|
| 8,620,730 | B2 * | 12/2013 | Cox | G06Q 30/0209 705/14.44 |
| 2009/0227925 | A1 | 9/2009 | McBean et al. | |

(Continued)

*Primary Examiner* — Michael A Keller

(57) ABSTRACT

A method and system to convert user activities performed in a real world into virtual world activity. The system includes a virtual world environment with a virtual activity tracker to obtain virtual activity performance data for an activity performed by a user in the virtual world environment; and a virtual world database to store the virtual activity performance data in a virtual profile of the user. The system also includes a real world activity tracker to obtain real world activity performance data for a real world activity performed by the user; and an activity convertor to convert the real world activity performance data into an amount of converted virtual activity performance data and add the converted virtual activity performance data to the virtual profile of the user.

17 Claims, 12 Drawing Sheets

(51) Int. Cl.
    *G09B 9/00*          (2006.01)
    *G16H 40/67*       (2018.01)

(56) References Cited

U.S. PATENT DOCUMENTS

| | | | |
|---|---|---|---|
| 2014/0188009 A1* | 7/2014 | Lange | A61B 5/1128 |
| | | | 600/595 |
| 2015/0094134 A1 | 4/2015 | Noyes | |
| 2016/0357251 A1 | 12/2016 | O'Neil et al. | |
| 2018/0293796 A1* | 10/2018 | Dubach | G01C 21/20 |
| 2019/0102947 A1 | 4/2019 | Lee et al. | |
| 2020/0111148 A1* | 4/2020 | Soni | G06F 3/013 |

* cited by examiner

INCORPORATING REAL WORLD PHYSICAL ACTIVITY INTO A VIRTUAL WORLD ENVIRONMENT

CROSS-REFERENCE TO RELATED APPLICATIONS

This application claims priority to and benefit of co-pending U.S. patent application Ser. No. 16/869,601 filed on May 8, 2020, entitled "INCORPORATING REAL WORLD PHYSICAL ACTIVITY INTO A VIRTUAL WORLD ENVIRONMENT" by Galasso et al., and assigned to the assignee of the present application, the disclosure of which is hereby incorporated by reference in its entirety.

The application Ser. No. 16/869,601 claims priority to and benefit of U.S. Provisional Patent Application No. 62/845,211 filed on May 8, 2019, entitled "INCORPORATING REAL WORLD PHYSICAL ACTIVITY INTO A VIRTUAL WORLD ENVIRONMENT" by Galasso et al., and assigned to the assignee of the present application, the disclosure of which is hereby incorporated by reference in its entirety.

FIELD OF THE INVENTION

Embodiments of the invention generally relate to methods and apparatus for incorporating real world physical acts into a virtual world environment.

BACKGROUND

Virtual worlds are growing in popularity. They includes games that are played on boxes in basements, courses that are navigated on exercise equipment, simulators, and the like. Moreover, as virtual worlds continue to be developed and become more realistic, immersible, and accessible, the use of virtual environments as training tools, user performance developers, testing grounds, and the like, will continue to be a breeding ground for invention, advancement, discovery, and development.

BRIEF DESCRIPTION OF THE DRAWINGS

So that the manner in which the above recited features can be understood in detail, a more particular description may be had by reference to embodiments, some of which are illustrated in the appended drawings. It is to be noted, however, that the appended drawings illustrate only typical embodiments of this invention and are therefore into to be considered limiting of its scope, for the invention may admit to other equally effective embodiments.

Figure 1:
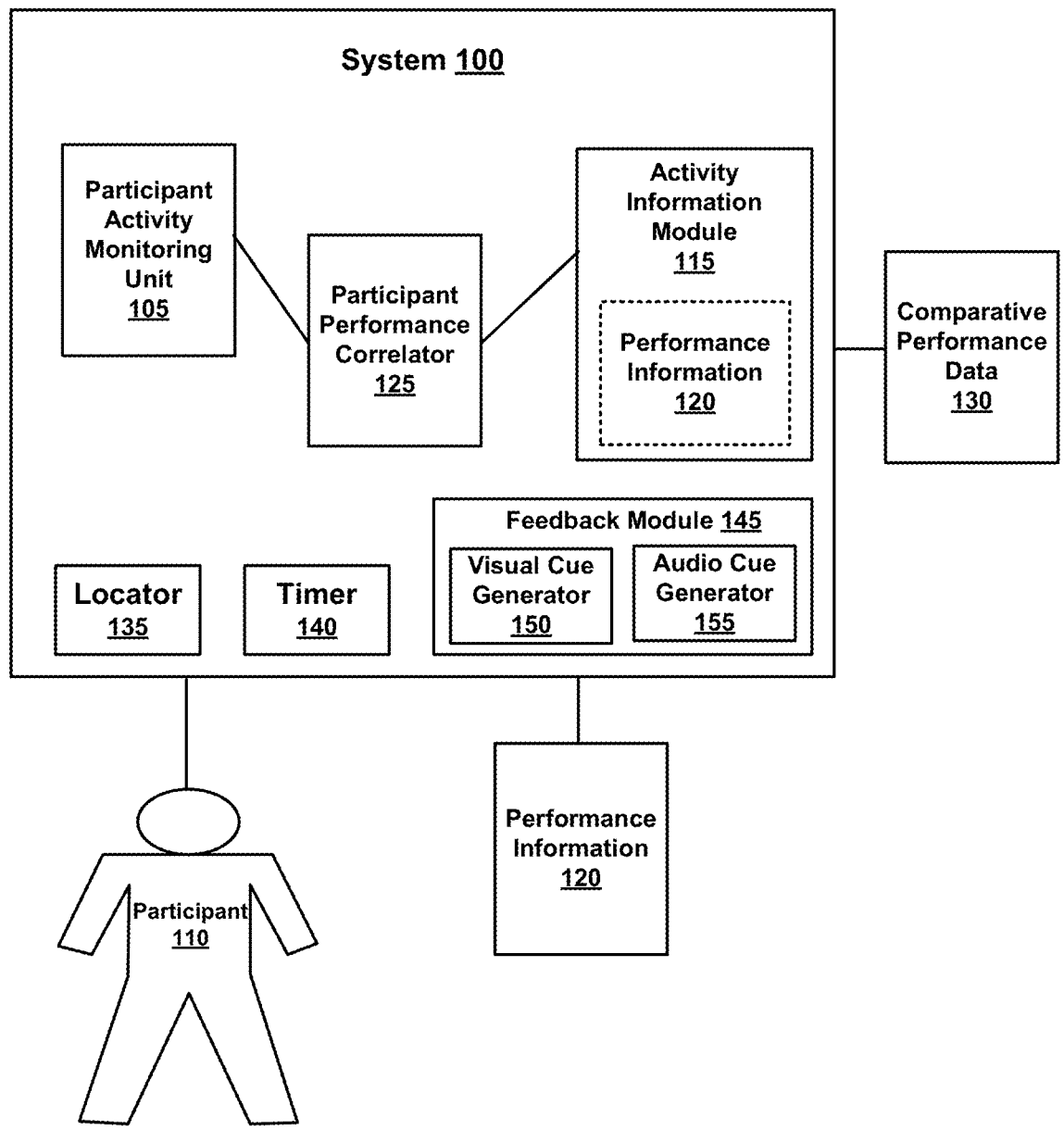
FIG. 1 is a block diagram of a system configured to be coupled with a participant of an activity, in accordance with an embodiment.

The drawings referred to in this description should be understood as not being drawn to scale except if specifically noted.

DESCRIPTION OF EMBODIMENTS

The detailed description set forth below in connection with the appended drawings is intended as a description of various embodiments of the present invention and is not intended to represent the only embodiments in which the present invention may be practiced. Each embodiment described in this disclosure is provided merely as an example or illustration of the present invention, and should not necessarily be construed as preferred or advantageous over other embodiments. In some instances, well known methods, procedures, objects, and circuits have not been described in detail as not to unnecessarily obscure aspects of the present disclosure.

In the following discussion the terms "real world" and "virtual world environment" are utilized.

For purposes of the following discussion, the term "virtual world" or "virtual world environment" refers to exercise and actions that a user does while observing a virtual world environment 1010. For example, in a motorcycle, flying, car driving, and the like virtual world environment, the user would be manipulating controls in a simulator or in a seat while the actual machine doing the performance would be virtual.

In contrast, in the "virtual world environment" of a bike ride, hike, run, walk, jog, stair climb, rowing, or other manually performable activity, the user would actually be performing the activities, but they would be presented to the user in a virtual world environment 1010. Using a bike as an example, the user would be working out on a stationary bike (or their actual bike mounted on a trainer stand), but instead of just seeing a window or wall, the virtual world environment would present the user's activity virtually to the user (e.g., via a GUI, virtual reality goggles, or the like). For example, instead of a ride in the living room, the virtual world environment ride would be a gravel road to a waterfall, a cross-country trail, a race (sprint, century ride, ultra-cycling race), downhill trail, etc. Thus, the user would be physically exercising, but the user would experience the exercise in the virtual world environment 1010.

The term "real world" refers to exercise and activities that a user does in the actual environment. For example, the user actually riding a gravel road to a waterfall, riding a cross-country path, riding in a race (sprint, century ride, ultracycling race), riding a downhill trail, etc.

Unless specifically stated otherwise as apparent from the following discussions, it is appreciated that throughout the present detailed description, discussions utilizing terms such as "receiving", "storing", "providing", "rating", "analyzing", "generating", "recording", "submitting", "correlating", "presenting", "selecting", "corresponding", or the like, refer to the actions and processes of a computer system, or similar computing device (e.g. electronic). The computer system or similar electronic computing device manipulates and transforms data represented as physical (electronic) quantities within the computer system's registers and memories into other data similarly represented as physical quantities within the computer system memories or registers or other such information storage, transmission, or display devices. Embodiments are also well suited to the use of other computer systems such as, for example, optical and mechanical computers.

Embodiments provide an interactive race system and method that will empower the local enthusiasts to race and compete, non-concurrently if desired, on their favorite local trails without the hassle of long travel, early morning registration times, limited course time, undue expense, crowded courses, governing body intrusions, and others setting the courses on which to compete. Embodiments provide a system and method empowering race enthusiasts to race and compete, non-concurrently, on world class racecourses and against professional athletes on those courses.

In general, embodiments hereof pertain to a system for delivering performance data regarding a participant's performance, or anticipated performance, of an activity. The system 100 of FIG. 1 is configured to be coupled with the participant and/or participant's vehicle. A participant activity monitoring unit monitors the participant's performance of an activity. For example, the participant's location, speed and power output may be monitored. Additionally, an activity information module stores information corresponding to or related to the participant's performance of the activity. For example, the activity information module may store data associated with a professional's performance of the same activity. Then, based on the participant's monitored performance and the stored professional's performance data, a participant performance correlator delivers comparative performance data to the participant. In one instance, this comparative performance data may come in the form of advice to the participant while performing the activity. Additionally, the data may include a rider's time or distance behind or ahead of a professional's [recorded] performance at any point on the course.

More particularly, and using an example of a mountain biker traversing a trail that has been catalogued in accordance herewith, embodiments hereof enable the mountain biker to receive pre-recorded audible advice during his ride, via for example a wireless ear piece or "bud," to improve his speed and/or technique over the trail. In one embodiment, system 100 is coupled with the mountain biker. More specifically, system 100 may be attached to the mountain biker's bike. In one embodiment the system 100 communicates with and receives data from, via wire or wireless components of the bicycle such as suspension performance sensors, power sensors, speed sensors, accelerometers, strain gages, and other suitable telemetry devices.

System 100 has stored thereon information regarding the trail as well as the performance data of a professional rider having traversed the same trail. Such data may be downloaded, in advance of a chosen ride, from a remote server, such as is located on the Internet, by connecting system 100 to a network and accessing a selected network address containing pre-recorded ride information catalogued by ride location (e.g. by selectable icon located proximate the recorded trail on a digital map) and downloading ride information associated with the chosen ride. As the mountain biker rides over his chosen trail, system 100 monitors parameters of the mountain biker and bike, such as location, speed, operating gear ratio, suspension usage, power output, etc.

System 100 may monitor any or all of the mountain biker's speed, location, elevation, distance traveled, power output and heart rate. System 100 may take measurements of any or all selected parameters at a user selected frequency or frequencies. Optionally, system 100 may calculate a rate of change of a given parameter and adjust a measurement and recording (sampling rate) frequency in response to the calculated rate of change. In one embodiment, system 100 increases measurement and recording frequency of a given parameter in response and proportion to a higher rate of change of that given parameter. Such increased frequency affords the increased data resolution required to represent the characteristic behavior of a parameter.

In one embodiment, the system includes a video camera for recording real time rider perspective and an audio recorder for recording real time rider impressions. All of the data recorded by system 100 is cross-correlated so that a given ride may be broken down incrementally with full data sets attributable to each increment. In one embodiment, increments correspond to sampling rate for a given data set such that incremental differences vary depending on the data set chosen for increment basis. In other words, for example, increments for elevation will each include a complete data set but the difference between recorded data points will be dictated by the frequency at which elevation was recorded.

Further to the example, a different data perspective may be had, viewing the same data set from the perspective of location, where the location data was changing at a different rate than elevation. The data set for the location will be complete for each "bread crumb" associated with that database. Additionally, each data point of elevation will also represent a complete data set. As such, the raw data for any data type may be in excess of the chosen increment for that data type.

In one embodiment, system 100 compares the mountain biker's progress with that of the professional rider's progress through the trail. Based on this comparison, system 100 is able to offer advice to the mountain biker during his trail ride. The advice is pre-recorded by a previous rider of the trail or trail segment and is triggered to be delivered to the current rider by system 100 based on the occurrence of a data input trigger in real time. For example, system 100 may warn the mountain biker of an approaching small steep hill and advise that the mountain biker should be prepared to shift into a lower gear and to increase his pedaling RPMs. Such a warning would be triggered by a GPS real time input that such a "steep hill" was upcoming. The GPS real time input would be derived from real time GPS data as compared, by system 100, to the previously downloaded GPS data (and location in advance of the steep hill) that gave rise to the advice during the recording run by the professional or other pre-recording rider.

Other useful information that can be correlated with actual trail position and elevation and delivered to the rider in advance includes but is not limited to: braking requirements; upcoming cornering events; jumps drop and offs; and natural obstructions such as rocks and logs. In one embodiment, the rider's physical parameters, including power output, are monitored and audio advice may include, but is not limited to: slow down; take an electrolyte supplement; and drink liquid. Such physiological advice may also be given in response to a location based on previously recorded rider experience. Such advise may be given in response to data from, for example, a power meter. In that event, a rider's maximum sustainable output wattage (or heart rate) may be known and when such amount is exceeded, the rider may be prompted to slow down.

In one embodiment, a rider may be instructed to slow down because a lower percentage of the rider's maximum wattage is required as a cap at a preliminary phase of the ride (in other words, system 100 "knows" what the rider must yet traverse and has calculated a power spread for the rider over the course and is warning the rider that the power output allotment for a given course section is being exceeded). In one embodiment, this advice may be given in the professional rider's voice via an ear bud (wired or wireless) or similar audio transmitter interfaced as an output with the system 100. In one embodiment, the advice may be displayed on a user display such as an LCD screen. In one embodiment, some or all of the advice may take the form of warning and go lights, associated with a display or device on the bike, such as, for example: a green light for proper RPM or speed in a given section; and a red light for too low an RPM or speed. If the rider is engaged in real time virtual competition with a previously recorded rider (or fabricated goal) goal performance ("chasing a rabbit"), a green light may indicate that the rider is even with or ahead of the goal and a red light may indicate that the rider is behind the goal.

In one embodiment the rider may choose the red light green light thresholds. For example, the rider may choose for a green light to show only if the rider is 10% faster than the performance goal being used. The "rabbit" performance is previously downloaded, with or without advice, and the rider's system 100 GPS (or other location provider) tracks the current ride in comparison to the pre-designated or recorded "rabbit" ride. In this manner, the mountain biker may feel as if he has received the best possible instructions and/or competition to improve his ride and from a professional whom he admires.

Additionally, one embodiment enables a participant's recorded performance of an activity to be uploaded to a website (or social media platform, app, or the like). At this website, the participant's performance may be compared to other performances of the same activity by the participant or by other participants. Based on these comparisons, advice may then be given to the participant via the website regarding ways to improve his performance of that activity. In one embodiment, riders may upload their performances over a given track or trail and view comparisons of their data with other riders' data sets. Such comparative data may be viewed graphically. Such data may be viewed incrementally so that varying comparative performance are apparent at different, for example, locations of the track. The data may be used to generate a virtual "race" using post run results for all contestants but showing contestants' results incrementally in "real race time" as generated from the compared data sets. In other words, the contestant riders may view, on a 3D trail map or split screen with actual video or incremental and changing parameter data, a race between the recorded run results (i.e. the contestants).

In one embodiment, a website may host a virtual race over a given period of time. For example, a race may be open for a month. During such month all certified race results are posted to the website. Results may be certified by encryption key stamped GPS encoded data or other comparable method where a rider checks in with the website, receives a download data key for attachment to a trail run file (where the key is activated for one time use by the rider and associated with a time stamped data run), activates the key prior to the run and ends the run directly after the ride (run), thereby certifying the GPS correlated run data with the upload race key. At the end of the open period (e.g. month) race results are posted by categories selected by the website (e.g. age, gender, trail, bicycle type) and winners announced. The website will include algorithms for comparing GPS (or other location) data to ensure that contestants in a given race all rode substantially the same course. Such algorithm can further check for large speed anomalies that may indicate non-conforming rider behavior (e.g. motor racing when bicycle was the call).

In another example, a skier races down a slalom ski run, swerving around five gates. System 100 monitors and records the skier's performance in relation to any or all relevant parameters. In one embodiment, a parameter includes beacons associated with geographic features, such as for example, the slalom gates and the system 100 includes a transponder for timing passages relative to such gates. In one embodiment, the system 100 includes a radio frequency identification tag (RFID) that records gate passage signals in the system 100. In one embodiment, the gate passage signals are correlated with time. In one embodiment, the RFID tag is passive, and a discreet RFID tag may be associated with each individual user. In one embodiment, the skier may receive advice directly, via audio and/or visual interface, from system 100 as to how fast to approach and how wide to turn around each gate. In one embodiment, the gate beacon or beacons may transmit advice data to the system 100 in real time and the skier may receive audio, visual or tactile input from the system 100 in response to the gate beacon transmission. In one embodiment, the gate beacons process data and generate transmissions to the skier (via system 100) based on real time interaction with the Internet. In one embodiment, physiological parameters of the skier and physical parameters of the ski (e.g. heart rate and ski flex respectively) are measured by sensors and factor into the advice given at various points on the course or run.

In one embodiment, the skier may upload his recorded performance data (stored in system 100 during run time) to a website configured for receiving this information, and compare his completed ski run to his previous ski runs or to other skiers' performances. The website may deliver advice to the skier, via computer interface, cell phone interface, or another suitable Internet user interface, to improve the skier's performance. In one embodiment, the advice may come in the form of technique advice and/or equipment selection, tuning and/or replacement. For example, a skier may be advised to change up his skis for a shorter pair, a more technically advanced pair, or a newer model that would be more appropriate for a particular ski run. Additionally, in another embodiment, the website may rate various skiers' performances over the ski run and select a winner.

Thus, one embodiment enables a virtual competition, within which a participant may participate on his own time, while still being able to compare his incremental and overall results and data with a larger groups' and other users. Furthermore, embodiments enable a participant of an activity to receive high quality advice from a professional, experienced in the particular run or condition, during the performance of that activity. In one embodiment, general conditions are experienced by professionals, such as, for example deep powder snow skiing, and a recording of advice or advisory signals are transmitted to system 100 when appropriate conditions occur in real time.

For example, a skier may be out during a heavy snowfall while using system 100 that is tuned into an appropriate web connection or local beacon for receiving real time mountain or weather conditions. System 100 may determine its location, and real web or beacon information correlated with that location may be transmitted to the skier advising the skier of the heavy snow cover or snow fall conditions and making recommendations associated therewith (even associated therewith in relation to a given ski run which the skier is traversing or comprising a warning such as "get off the mountain and seek shelter").

Moreover, embodiments recommend equipment replacement and upgrades to participants, based on their performances, to help improve the participant's overall performance, thereby enhancing revenue generation for the maker and/or seller of the equipment. In one embodiment, equipment or service providers in a given sport may pay for, and web (or app) hosts may sell, space (virtual web site space) for posting data and information that are useful to trail users so that the providers advertising information may be transmitted therewith. As mentioned previously, tuning characteristics for mountain bike suspension and advice pertaining thereto may be broadcast to a rider of a particular run or trail. In one embodiment, a user may key in a chosen catalogued run or trail or portion thereof and receive advice in advance of executing the run or trail.

Example Architecture of System 100

One embodiment includes a hosted and administered competition website designed to accept information from and integrate with commercially available navigation satellite system (NSS) or other local, regional, national, etc., terrestrial and/or satellite navigation technology as discussed herein.

Referring now to system 100 of FIG. 1, one embodiment includes a participant activity monitoring unit 105 for monitoring a performance of an activity being performed by a participant, an activity information module 115 for storing performance information corresponding to the activity and a participant performance correlator 125 for delivering comparative performance data based on the monitored performance of the activity by the participant and the stored performance information. For example, the participant activity monitoring unit 105 may determine the geographic position of system 100 while an activity is being performed In the following discussion, the term "geographic position" (or location) means the determining in at least two dimensions (e.g., latitude and longitude) of the location of system 100. In one embodiment, participant activity monitoring unit 105 is a satellite based position determining system and receives navigation data from satellites via an antenna or other signal receiver. In one embodiment, the antenna is remote from the participant activity monitoring unit 105 ("PAMU 105") and communicates therewith via a local wired or wireless preferably low power protocol. Such a remote antenna facilitates communication with satellites (or using terrestrial navigation aids) in the event that the actual PAMU 105 is out of clear satellite view. In use, such a remote antenna may be placed on the participant or vehicle at a location that more often has a clearer satellite view than the PAMU 105. In one embodiment, an antenna/local beacon, that communicates with the PAMU 105, may be placed on a hilltop or other area, having a clear satellite view, proximate a trail or track to be ridden. In one embodiment, three spaced antenna/local beacons may be used and the PAMU 105 includes a position differentiator for triangulating from the local antenna/beacons and combining such data with satellite data from one or more of the antenna/beacons to establish a net location calculation set for the trail run. Examples of position determining systems include local, regional, national, and/or global systems that are terrestrial, satellite, and/or hybrid systems, such as for example, cell tower triangulation, as well as ground-based position determining systems, or other satellite-based position determining systems such as Global Orbiting Navigation Satellite System (GLONASS), Compass/BeiDou, Galileo system, and the like.

Additionally, system 100 may be well suited to utilize a variety of terrestrial-based position determining systems. For example, terrestrial based broadcast signals such as LORAN-C, Decca, and radio frequency beacons may be utilized.

While examples herein refer to an "activity" as mountain bike courses and virtual interactive competition, the disclosure hereof is equally suited for use to facilitate a wide variety of competitive events/activities such as, but not limited to, running, swimming, motor vehicle sports, boating (e.g., sailing), rock climbing, mountain climbing and any other suitable competitive sport comprising either point to point or closed loop type competition or combinations thereof. The disclosure herein is also suitable to facilitate time/location finding events/activities such as, but not limited to, rally racing, enduro racing, orienteering, and the like.

Referring still to FIG. 1, in one embodiment PAMU 105 is coupled with a locator 135 and/or a timer 140. The locator 135 determines the location of the participant 110 during an activity. The timer 140 monitors a time of a location of the participant 110 during an activity.

In another embodiment, activity information module 115 stores performance information corresponding to the activity that is being performed and which is being monitored by participant activity monitoring unit 105. Performance information 120 is information that is related to the activity that is being monitored by the participant activity monitoring unit 105. For example, if the activity is a mountain bike trail ride, then the performance information 120 that is stored in system 100's activity information module 115 may be, but is not limited to, information relating to shocks (e.g. spring rate, damping rate, pressure, travel velocity, pressure differential, force, displacement), cadence, velocity, gear positioning, athlete power output, suspension, and the heart rate of the participant. In one embodiment, such performance data enters the data storage set as correlated with location and time and other data on an incremental basis so that analysis may be performed incrementally stepwise through the run.

Further, the performance information 120 may also be one or more prior performances of the activity by the participant 110 and/or someone else. Information recorded from the prior performances may also include course layout registration for local, regional, national, and global courses, and provides the timing system for competitors on registered courses. Additionally, performance information 120 may also be stored instructions relating to the activity. Of these stored instructions, selected instructions may be delivered to the participant 110 (e.g. audibly, visually, tactilely), based on the participant 110's monitored performance of the activity. All of the foregoing data types and instruction types may be stored incrementally for analysis or delivery at chosen increments (e.g. time, location, gear position—increments of a chosen baseline data type).

One embodiment includes a feedback module 145. In one embodiment, the feedback module 145 includes a visual cue generator 150. In yet another embodiment, the feedback module 145 includes an audio cue generator 155. A visual cue generator 150 provides a visual cue to the participant 110, such as but not limited to, a flashing light, a colored light, a series of colored lights, etc. The audio cue generator 155 provides an audio cue to the participant 110, such as but not limited to, a siren, a beep, a series of beeps, a voice, multiple voices, etc.

Figure 2:
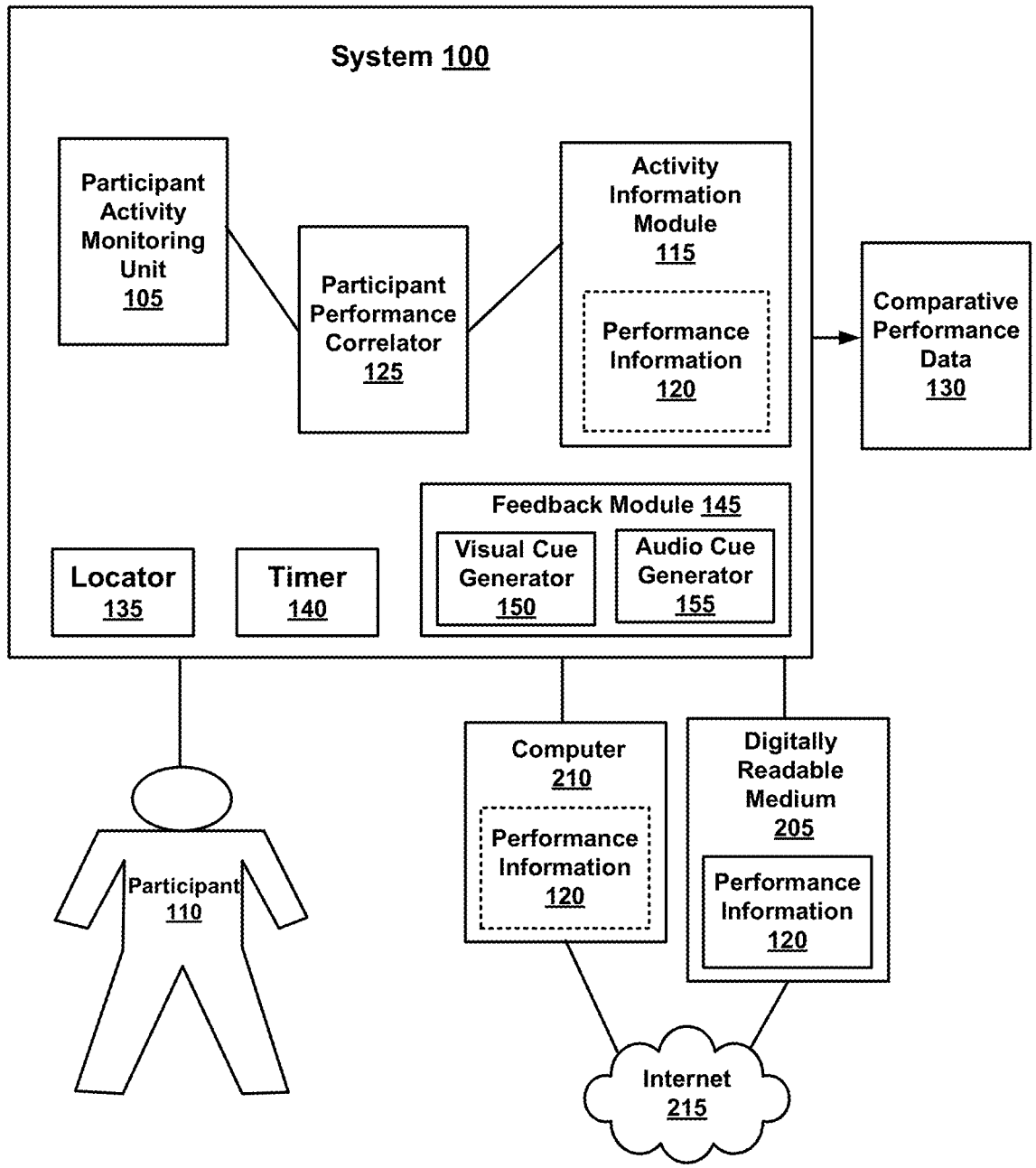
FIG. 2 is a block diagram of a system configured to be coupled with a participant of an activity, in accordance with an embodiment.

Referring now to system 100 of FIG. 2, in one embodiment, system 100 may be coupled with a computer 210, wired and/or wirelessly. In another embodiment, system 100 may be coupled with a digitally readable medium 205, wired and/or wirelessly. The computer 210 may access the digitally readable medium 205 via the Internet 215, and vice versa.

The digitally readable medium 205, such as for example a server with a memory device, provides course layout registration for local, regional, national, and global courses, and provides the timing system for competitors on registered courses.

In one embodiment, cycling computers with a location defining capability may be utilized to provide traces of proposed competition courses. These cycling computers are also used for providing timing for the courses on which a participant wants to compete. In one embodiment, GPS equipped cell phones may be used to gather GPS and other data and, with properly written application programming, to function substantially as an embodiment of system 100 (including audio instruction output and ear bud interface). In one embodiment, local groups or individuals can contact the virtual race competition, or as referred to herein, a "virtual racecourse" (VRC) administrators to have a course registered as an authorized and supported competition venue. In another embodiment, a competition venue will have criteria for registering a course. In one embodiment, the option of registering a course will be for legal trails only. In one embodiment, a course may not have any speed limit thereon. An NSS (or other location tracker) trace of the course may be submitted, including registering start and finish points. This course may be a point to point or a closed course loop. In one embodiment, such as for example, auto rally, orienteering or moto-enduro, a course may have speed limits through various legs (between check points) and the system 100 is used to verify compliance such that the rally style race may be run in non-concurrent space as described herein referring to other racing such as mountain bike racing.

Thus, one embodiment provides a system for comparing the performance of an activity by a participant with the stored performance information corresponding to the activity. Based on this comparison, comparative performance data is delivered to the participant and/or one other than the participant. Based on this performance comparison, a participant may then receive feedback during or after the performance of the activity. This feedback may take the form of visual and/or audio cues.

Example Operation of System 100

More generally, in one embodiment, system 100 is utilized to provide comparative performance data 130. More particularly and referring now to 300 of FIGS. 3a and 3b, a flowchart of a method for performance comparison of multiple performances of an activity is shown. In one embodiment, process 300 is carried out by processors and electrical components under the control of computer readable and computer executable instructions. The computer readable and computer executable instructions reside, for example, in data storage features such as computer usable volatile and non-volatile memory. However, the computer readable and computer executable instructions may reside in any type of computer readable medium. In one embodiment, process 300 is performed by system 100 of FIG. 1.

Figure 3A:
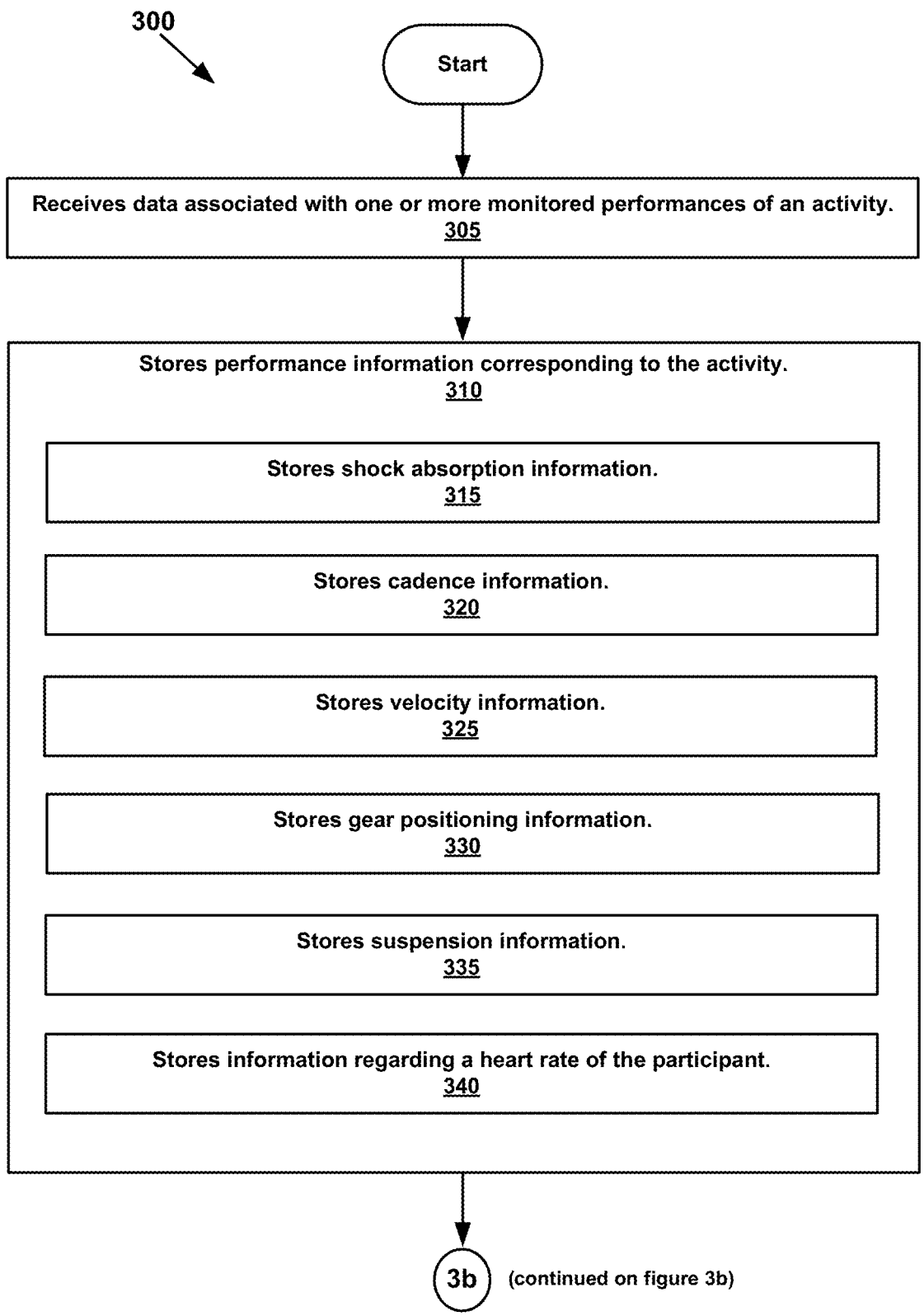
FIGS. 3a and 3b combine to form a flowchart of an example method for performance comparison of multiple performances of an activity, in accordance with an embodiment.

In one embodiment, data associated with one or more monitored performances of an activity is received at the digitally readable medium 205, as is described at 305 of FIG. 3a. In another embodiment, performance information corresponding to this activity is stored at the digitally readable medium 205, as is described at 310 of FIG. 3a. Then, comparative performance data is provided to a participant of the activity based on the comparison between the received data and the stored performance information, as is described at 345 of FIG. 3b.

For example, in one embodiment, once a course is registered, competitors can run the course on their own time, as long as they have a compatible and an authorized location tracking device. The trace of their competition run will be compared to the trace of the registered run to make sure the same exact course was run. Each new competitor is given an icon for that particular course.

A live run feature can be run on the website where the interested competitor can run their icon versus other chosen rider's icons down the course. In this manner, the interested competitor may interactively visualize at which point he/she is faster, or the other riders are faster at specific sections of the course.

Figure 6:
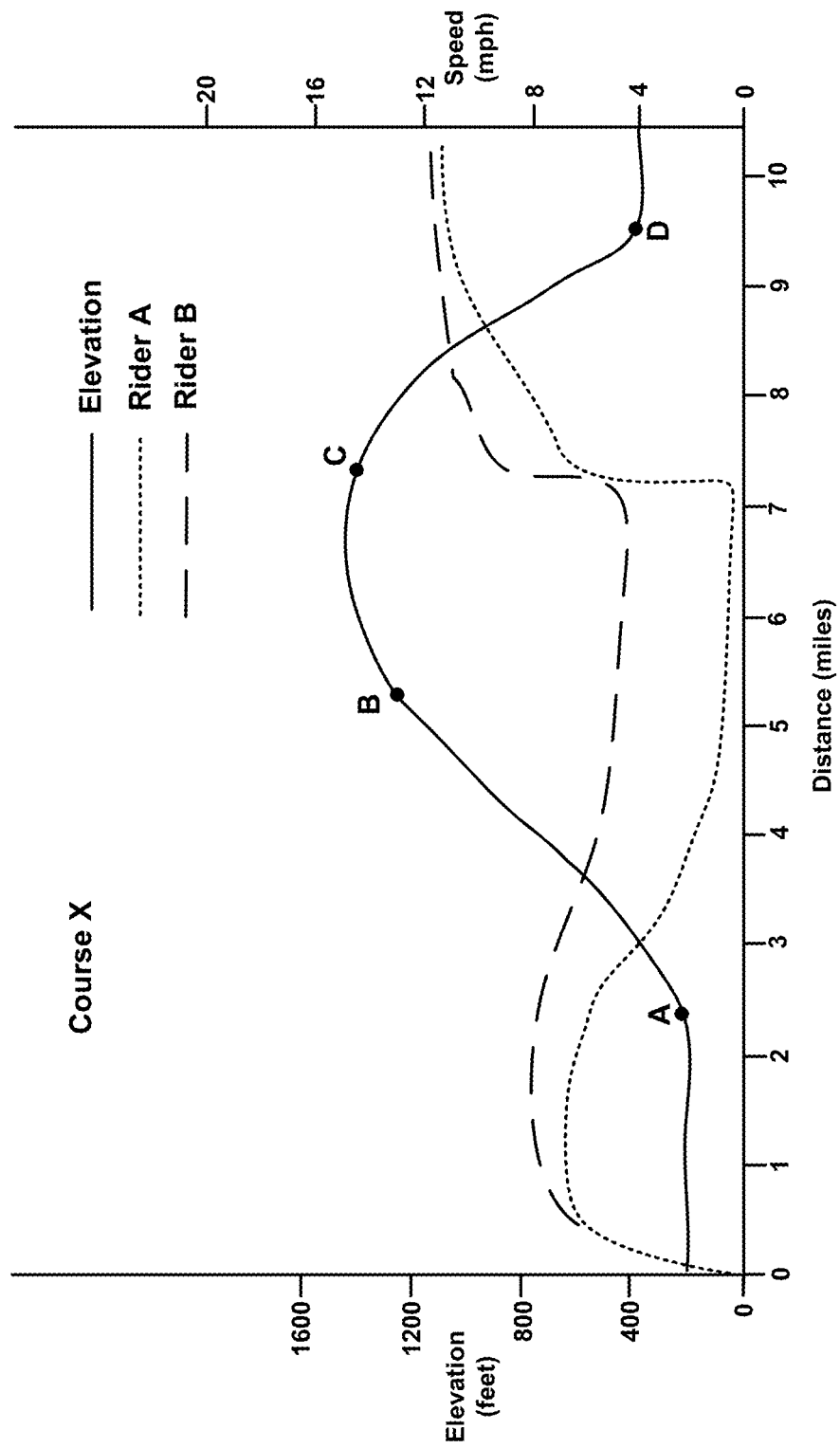
FIG. 6 is a graph measuring the speed, elevation and distance traveled by two bicycle riders, in accordance with an embodiment.
Figure 7:
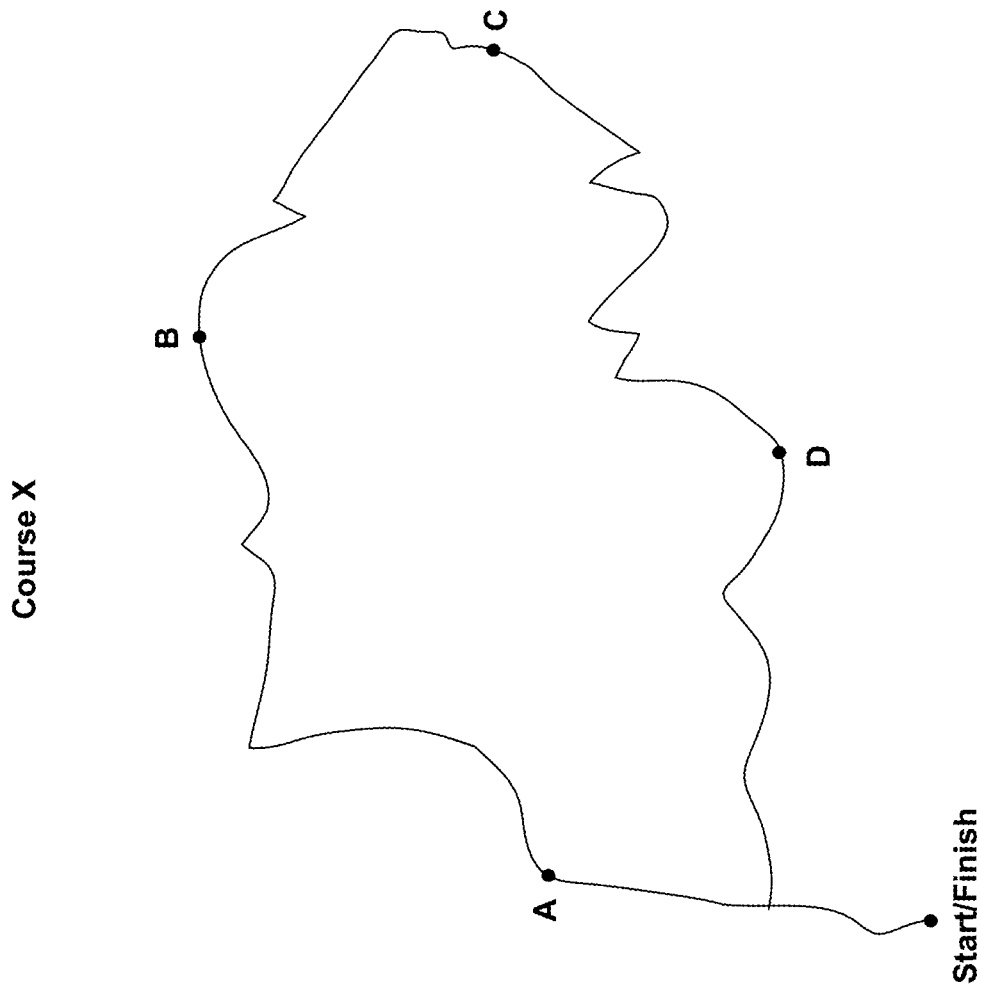
FIG. 7 is a trail map of the trail the two bicycle riders traversed as shown in FIG. 6, in accordance with an embodiment.
Figure 7:
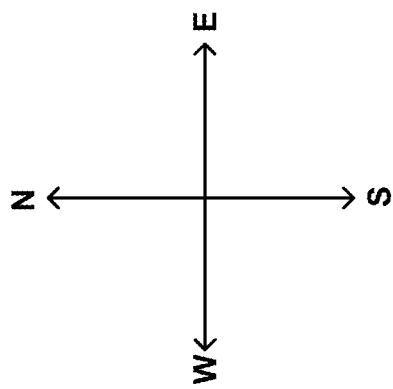

For example, and referring now to FIGS. 6 and 7, a map of a bicycle trail, Course "X", and a graph of the bicycle rides of Rider A and Rider B on Course "X" are shown. FIG. 6 considers the elevation, speed and distance traveled by the riders. Course "X" is a registered course. Rider A has an authorized location tracking device (a participant activity monitoring unit 105). Rider A rides the course. Rider A then uploads the data associated with his monitored ride performance onto a computer 210. Computer 210 communicates Rider A's Course "X" ride, either via wire or wirelessly, to the digitally readable medium 205. The digitally readable medium 205 compares Rider A's Course "X" ride to the registered Course "X" ride (not shown), to determine if Rider A stayed on Course "X" during his ride.

Furthermore, FIG. 6 also shows Rider B having also ridden Course "X" and having uploaded her information to a computer that communicates, wired or wirelessly, to the digitally readable medium 205. (Rider B also has an authorized location tracking device.) Rider A is now able to compare his ride to that of Rider B, and vice versa. Overall, Rider B finds that her ride was faster than Rider A's ride. As can be seen by the elevation vs. speed depiction in FIG. 6, Rider B was able to travel uphill at greater speeds than Rider A (between point "A" and point "C"). Furthermore, FIG. 6 shows that particular points along its graph, "A", "B", "C" and "D" match up with particular points, "A", "B", "C" and "D" on FIG. 7's Course "X" trail map. This point to point correspondence between the graph of FIG. 6 and the trail map of FIG. 7 enable a rider to determine his/her location within Course "X" itself.

Figure 3B:
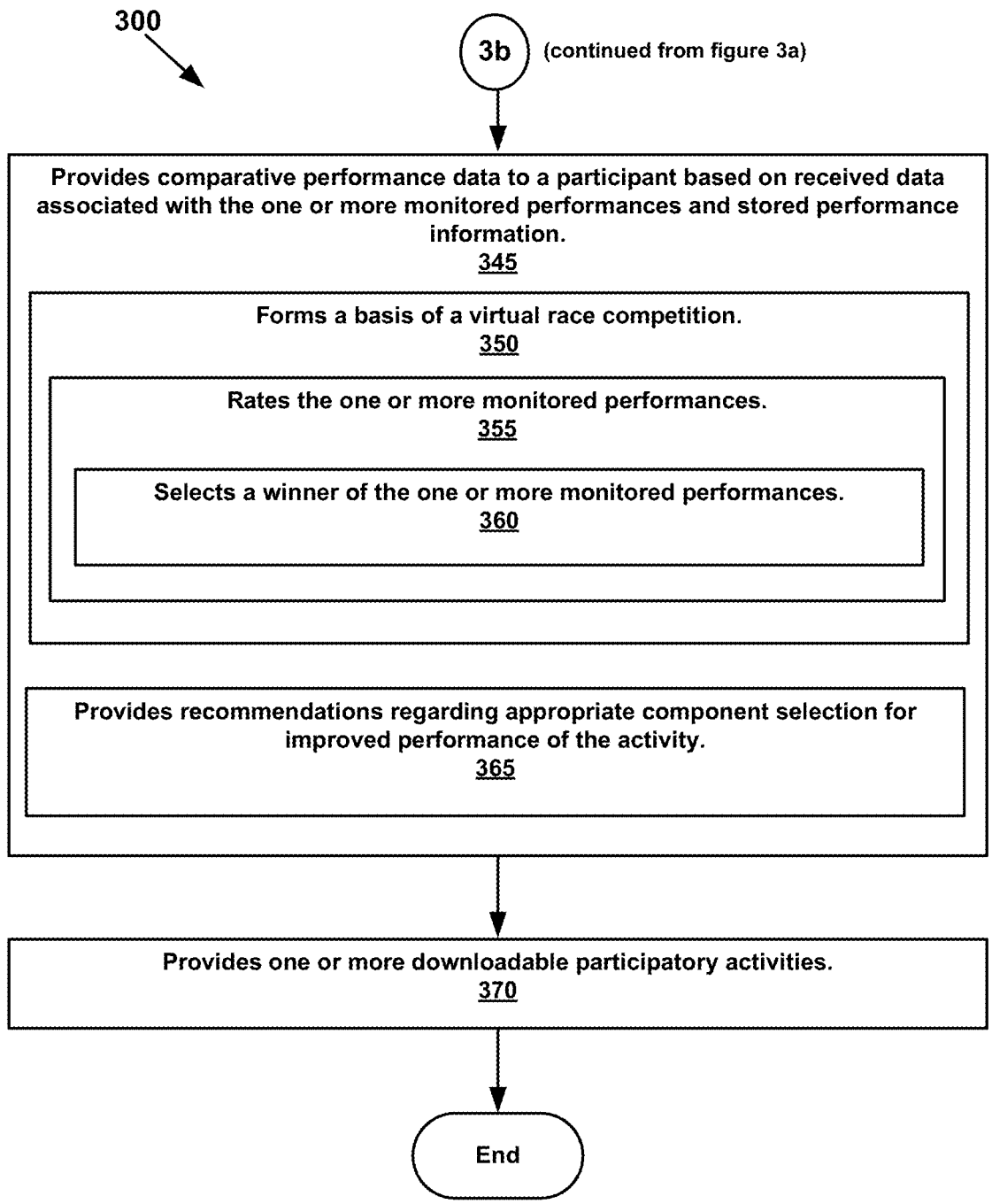

Additionally, and referring to 370 of FIG. 3b, one or more downloadable participatory activities is provided by the digitally readable medium 205. For example, in terms of mountain biking, a downloadable participatory activity is a course on which it is legal to mountain bike. It should be appreciated that a downloadable participatory activity may be any activity that is capable of being monitored by system 100. The digital readable medium 205 holds the course map and information relating to that course map for, such as but not limited to, data relating to an expert's ride through the course. In one embodiment, the participant 110 may download information relating to Course "Q" onto his/her system 100 at the activity information module 115. In this manner, participant 110 may use system 100 to enjoy riding Course "Q" without having to participate in a race with hundreds of other bicyclists. The participant 110 may also compare his/her ride to that of the expert's.

Referring now to 350 of FIG. 3b, one embodiment forms the basis of the VRC. In one embodiment, the VRC administrators will send out professional athletes with helmet cams and authorized location tracking devices to execute a fast course run time over a given registered course and to video the course during the run. Any course runner with access to a location tracking device can capture his or her own run of the given course and submit that to the Internet website for posting. Over time, run data accumulates for given courses, and participants can compare their results with others who have run the course (including professionals). Additionally, participants can review specific paths or "lines" chosen by other competitors who submit video (e.g. helmet cam) course data with their run. In this way, the nonprofessional rider can compete head to head in the VRC world, and can review the line selection of the professional rider.

In one embodiment, a single participant performs one or more monitored performances. In another embodiment, a plurality of participants performs one or more monitored performances. In one embodiment, a participant may run against their own performance or the performance of others by downloading the pre-recorded performance to system 100 prior to their ride. In one embodiment, a participant may "pre-ride" a course in virtual space by reviewing the pre-recorded ride data log, including video (and audio) of others. In one embodiment, a participant may critique his own ride by reviewing the recorded ride data log.

In one embodiment, the location tracking device are equipped with an algorithm allowing storage of course information and the time data associated with the traversal of a designated course. In one embodiment, the system disclosed herein derives course location data and associated speed/acceleration/altitude data (in one embodiment as a correlated data set) from algorithms within the location tracking device.

In one embodiment, the location tracking device is equipped to time and date stamp and "sign" with an encrypted verification code, data sets as they are generated. As such, in one embodiment, only verifiable data may be uploaded to the Internet site (because the site screens incoming posts for verification codes generated by the recording location tracking device).

In one embodiment, a host website hosts many different types of courses and many different types of events. A user can be matched to a desired sport/competition or other relevant classification or sub-class of activity or location (or other) by answering an initial query (e.g. choosing an object from an object set identifying the activity and sub-activity) upon entering the web site.

In general, almost any form of competition may be adapted to use with the VRC network system as disclosed herein. Additionally, competitors may post their profiles and other pictures and videos as they prefer. The VRC network functions to facilitate not only competition among athletes with similar interests but also serves as a social and networking site in facilitating communication among competitors (including individually identified personal or social networks). Optionally, participants can operate in a virtual competition world using location tracking device generated data or other profile data.

Another sport suited for use with system 100 is motocross. Motocross is a very popular sport. Open practice session track days are well attended, but many individuals shy away from the very confrontational aspects of real time track racing. Open practice "track days" are days held open by racecourses in which no actual race is scheduled. Therefore, riders (or drivers) may pay a fee and run the course for practice and improvement. The intimidation of a starting gate with up to 40 riders all heading into the first turn together keeps many riders from competing on actual race days. A motocross rider not wishing to experience the full blown race with line up start may race virtually using VRC. The VRC administrator can register various motocross tracks so that all a rider needs is an authorized (e.g., equipped in accordance with the disclosure herein) location tracking device mounted on their motorcycle, and they can compete on their local course at their discretion regarding time and circumstances. Such competition data can then be uploaded to the web site for comparison against others on the same track.

Again, professional riders can post times that they have run on these local and regional tracks along with video taken from a helmet cam. Using embodiments herein, the local amateur can compete against the professional rider. Thus, any day the track is open and any time of that day, the competitor can log a course run. Examples of sporting events that can be held using the VRC as disclosed herein are, but not limited to, the following: road racing track days; off road motorcycle riding; sailing (e.g. point to point or course type regatta); skiing; snowboarding favorite runs; trail running; and swimming.

The VRC can also be utilized as a virtual gym. For those who do not wish to compete against others but want to keep accurate track of their workout progress, the VRC can be utilized as a training log (e.g., weight training). This application focuses more on the website and less on the enabled location tracking device.

In one embodiment, the VRC site can also tie all these competitors and training athletes together with tech tips, equipment reviews, set up tips, course reviews, racing line chat, training tips, etc.

In one embodiment, popular courses with strong reviews can be visited by other enthusiasts from around the globe. The VRC system will seek travel and destination location activity from enthusiasts from around the world to tie in posting times and competition on courses they have only read about. In one embodiment, course run data, location data and user generated video data are associated with a broader inquiry web site such as a map or travel web site and users may virtually "ride" courses (or ski runs or experience the appropriate athletic endeavor virtually) before choosing to travel to them. As such, a user's "racing" or other athletic activity can be tied into vacation plans.

In one embodiment, established riding venues like destination bike parks can register specific runs and/or specific sections of favorite runs tied together. Vacation visitors can post times on these courses or propose new ones to the VRC system. This same thing applies to ski/snowboard areas. Amateurs can run (e.g. bike) sections of the Tour de France, and can compare their times to the stages and times actually raced.

Referring now to 355 of FIG. 3b, in one embodiment, one or more of the monitored performances is rated. Referring now to 360 of FIG. 3b, in another embodiment, a winner of the one or more monitored performances is selected. For example, the VRC for those groups wishing to take things further can establish qualifying events to end up with championships and champions. For example, the champions can be crowned for, but not limited to, the following: most rides in a given time; the most courses run in one year; the most vertical feet climbed; and the most vertical feet descended (altitude data component).

In one embodiment, the VRC system will track stats on enthusiast user activity, which will be available to product leaders in the various activities. Thus, in one embodiment, the VRC system provides opportunity with vacation/travel companies, destination locations, Original Equipment, and After Market manufacturers. For example, a user will procure a location tracking device that is further equipped with the capability of gathering course traversal data, corresponding time and corresponding altitude and generating a data set that is time date stamped and verified. The user will then enter the Internet (or suitable network) and request a new course registration if applicable, or existing course add run if applicable. The user will upload a verified data set for the chosen course (following new course registration by the website if applicable) and any other peripheral information such as weather stats, course condition, comments, video, etc. The user may choose to create a personal profile space, add a link to her course run to her existing profile, or the like.

In one embodiment, the upload process occurs via, for example, but not limited to, a wireless link between the location tracking device and a personal computer/terminal/mobile device of the user. The personal computer is in turn connected to the Internet via a suitable connection medium. Optionally, the data is loaded into the computer (digitally readable medium such as hard drive) and uploaded to the Internet at a later time. Following upload, the user may view her results as compared with others who have traversed the same course and may also post comments.

In one embodiment, the course page itself includes a link whereby users can post comments, photos and other information regarding the course (e.g. a "blog"). Additionally, the website (or websites, app, social platform, or a combination thereof) includes a larger general blog or blogs regarding various sporting types and topics. The website posts the users' latest results and queries other results from the same course and then files users in appropriate place ranking (e.g. based on the fastest run times). In one embodiment, users may blog and post comments regarding their own or other users recorded data sets for given trails/runs. In one embodiment, other persons may now view the user.

Referring now to 365 of FIG. 3*b*, in one embodiment, recommendations regarding appropriate component selection for improved performance of an activity is provided. Furthermore, and referring to 315, 320, 325, 330, 335, and 340 of FIG. 3*a*, the following information may be stored at activity information module 115, respectively: shock absorption, cadence, velocity, gear positioning, suspension, heart rate of the participant, and the like. (Of note, this is not an exhaustive list of possible information that may be stored.) For example, and referring again to FIGS. 6 and 7, based on the riding performance of Rider A throughout Course "X", recommendations geared towards improving Rider A's performance may be made. For instance, as can be seen on FIG. 6 with reference to Rider A, between the points "A" and "C", Rider A slowed significantly in the face of a steep uphill climb. In one embodiment, participant activity monitoring unit 105 also monitors factors such as gear positioning, the heart rate of the participant, calories burned, etc.

Thus, one embodiment will recommend, (based on one or more aspects of the Rider A's performance and stored data relating to gear positioning as well as elevation, velocity, and distance), that Rider A should change up his/her gear positioning technique. Furthermore, a new gear, suspension component, tuning (e.g. adjustment) state, or the like, may be recommended to Rider A thereby increasing Rider A's speed during ride time. Furthermore, one embodiment will recommend new shocks or other components based on Rider A's performance.

Figure 4:
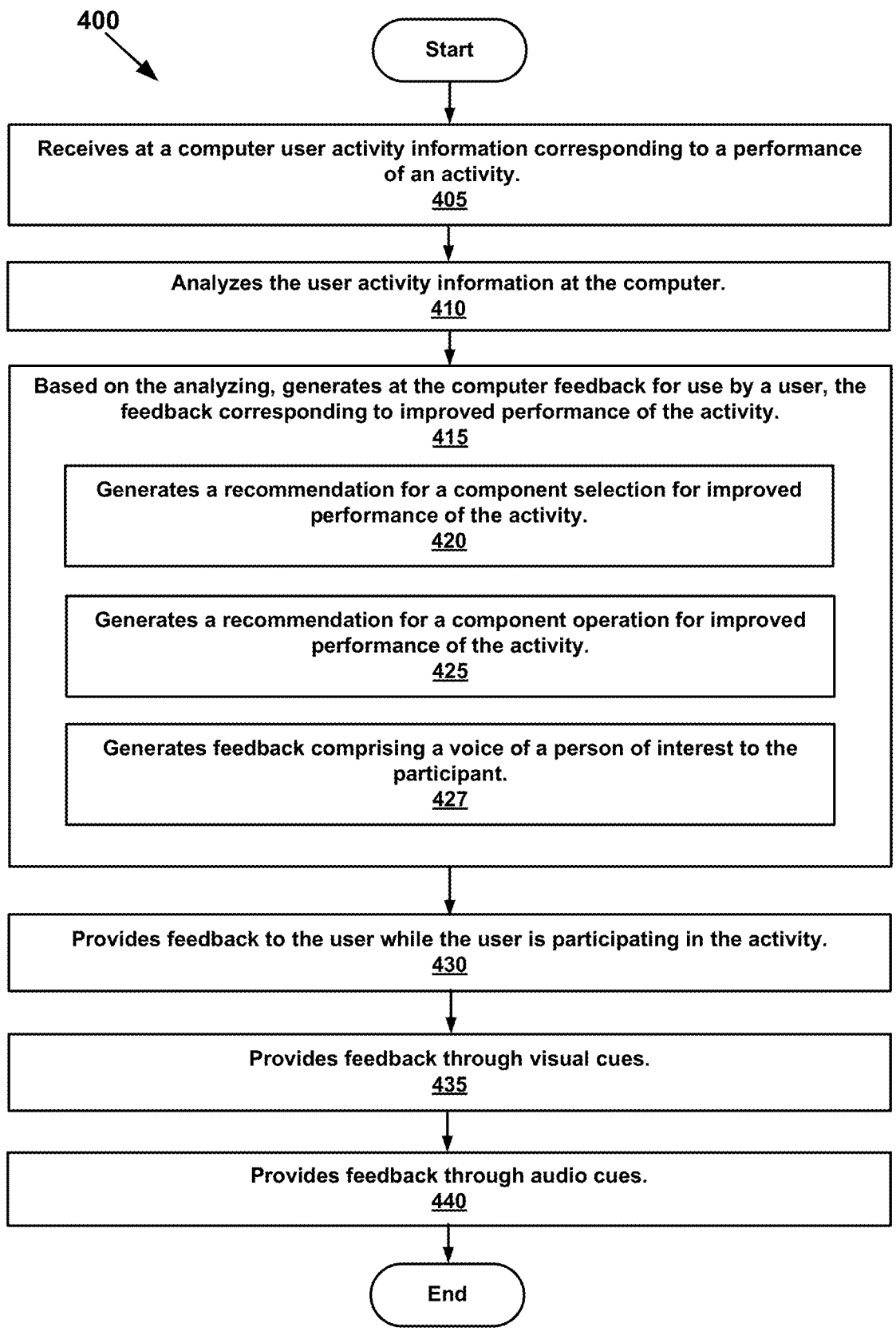
FIG. 4 is a flowchart of an example method for enhancing revenue generation, in accordance with an embodiment.

Referring now to 400 of FIG. 4, a flowchart of a method for enhancing revenue generation is shown. Referring now to 405 of FIG. 4, in one embodiment, user activity information corresponding to a performance of an activity is received at a computer. Referring now to 410 of FIG. 4, in one embodiment, the user activity information is analyzed at the computer. Then, and referring to 415 of FIG. 4, based on the analyzing of 410, feedback is generated for use by the user at the computer. The feedback corresponds to improved performance of the activity.

For example, and referring to 420 of FIG. 4, feedback can include a recommendation for a component selection for improved performance of the activity. As described herein, this component selection may be for new shocks, an updated suspension system, alternate equipment, etc. Further, and referring to 425 of FIG. 4, in one embodiment, feedback will include a "coaching" style tip or recommendation for a component operation to improve performance of the activity. For example, a rider may be told that he/she should switch into higher or lower gears more quickly and at particular points in time during climbing and descending a steep hill in order to improve overall speed.

Referring now to 430 of FIG. 4, in one embodiment, the feedback is provided to the user while the user is participating in the activity. In one embodiment, the user receives the feedback directly from system 100. In another embodiment, the user receives feedback through a device local to the user for promulgation to the user. For example, the device may be, but is not limited to, an earpiece coupled with system 100 and configured for capturing sound from the system 100 and delivering that sound to the user. In one embodiment, and referring to 435 of FIG. 4, the feedback is provided through visual cues. In another embodiment, and referring to 440 of FIG. 4, the feedback is provided through audio cues, haptic cues, or the like.

In one embodiment, and referring to 427 of FIG. 4, the feedback that is generated is a voice. In one embodiment, the voice is that of a person of interest to the participant. For example, the person of interest may be an admired professional of the activity, or a fan favorite. In one embodiment, the person of interest may be anyone whom the participant wants to hear speaking to him/her before, during or after the performance of the activity.

In one embodiment, for example, mountain biker Bob has never ridden any trails or raced any courses in Fantasia. He has heard, however, that the riding and racing in Fantasia is spectacular and challenging. He has heard of several racecourses in Fantasia and he sits down at his computer system (e.g., desktop, laptop, tablet, mobile device, phone, or the like) to check it out. He connects to a website that includes a user navigable map having icons associated with geographic locations thereon. He navigates to a map of Fantasia and specifically to a racecourse used for an annual mountain bike race called the "Skyline."

In one embodiment, there are many pre-recorded runs of Skyline associated with visible and active icons on the map. Bob selects an icon and a menu appears that includes choices such as: Ned Pete Skyline run no. 1 video, Ned Pete Skyline run no. 1 audio, Ned Pete Skyline run no. 1 altitude and location data, Ned Pete Skyline run no. 1 bike data, Ned Pete Skyline run no. 1 body data, Ned Pete Skyline run no. 1 with terrain enhancement (option allowing terrain map data to enhance video data as needed to make the recording play complete), select combination, all. Bob selects video, audio, altitude and location data. A menu then appears with the options "download" and "play."

Bob selects play (had he selected "download" he would have been prompted to designate a destination for the files at which point he could have selected a system 100 connected to his computer system). Bob watches the video and listens to the audio of Ned's race run. While observing a screen-in-screen inset showing Ned's position on the racecourse trail map. Bob watches the video several times, so much so, that he feels he is getting the course "wired." Bob is gaining the mental experience and reinforcement, regarding the racecourse, without ever having ridden Skyline.

In one embodiment, for example, mountain biker Bob decides that he wants to participate in the annual mountain bike race, "Skyline". Skyline is a 20 mile race over varied terrain. Bob designs a training schedule for himself in preparation for the race, aided by the sage advice he has already heard from Ned Pete. To help himself with his training, Bob purchases from his local bike shop a system 100. Bob then connects his system 100 with a digitally readable medium (e.g. server on the Internet) via his computer and downloads performance information relating to the Skyline race into his system 100. This performance information includes various data, instructions and pep talks from Ned Pete, a famous mountain bike racer.

In one embodiment, Bob attaches system 100 to his handlebars of his bicycle, turns on his wireless earphone, and begins training. As Bob warms up, by riding the one mile from his car to the beginning of the trail, he hears system 100, in the voice of Ned Pete, giving him a pep talk about the Skyline race. For example, Bob hears, "This is a very challenging race over really rough terrain, but I know that you can do it! I'll be with you at every turn. I'll tell you when you should hammer it and what gears to crank." Bob then makes it to the beginning of the trail. He stops his bike, sets his watch, and then starts. Immediately, he hears Ned say "Great start! Keep it moving . . . You've got a sharp corner coming up to your left with a log. Bunny hop and kick-out to your right. The trail cuts down to the left . . . Great job. You're on target." Bob appears to have begun his trail ride with great success.

In one embodiment, Bob begins to pour it on early in the course and is running ahead of his "rabbit." Everything is looking good when suddenly Ned's voice alerts, "you need to slow up a bit because your current pace is unsustainable." Bob has a heart rate monitor and a power meter rear hub. The data from those devices compared with the current location on the Skyline run, allow system 100 to trigger an alert based on known physiology of Bob and/or of athletes generally or a suitable combination thereof (e.g. a human in good condition is capable of outputting a sustained approximately ½ horsepower). If Bob is dramatically exceeding a known physiological parameter or his heart rate is anaerobic or his blood oxygenation is dropping dramatically (with an oxygen sensor), the system 100 might assume it was an end race sprint. The system 100, however, will alert Bob if he is too far from the end to sustain his activity level though the remaining course.

Later on in the ride, Bob starts to fall behind his chosen "rabbit" pace. System 100 has calculated the difference between the rabbit and Bob's performance and when the difference reached a predetermined (e.g. chosen by Bob) threshold it triggered an audio signal. He hears Ned state, "Get moving! You're falling behind." Simultaneously, a red light illuminates on the face of (or another type of feedback is provided by) system 100 making it clear that Bob is behind his "rabbit" pace. "Pay attention to your gears and your pedaling. You've got about half a mile of downhill coming up. Let's make up time. Lots of jumps. Get big air." Later on, Bob hears, "You're dialed in! Great job" Concurrently, the light on his system 100 is glowing green indicating he is even with the pace. Bob finishes the trail course in fairly good time, two and one-half hours. Bob then goes home and downloads the data associated with his monitored performance to the website. The next Saturday, Bob plans on riding that same course again, and comparing the new results with his time of two and one-half hours.

In one embodiment, system 100 may already have Ned Pete's voice with stored instructions that are ready for delivery to a participant. In another embodiment, these instructions may be downloaded to system 100 from remote server accessed using the Internet. Furthermore, there may be instructions and advice for various skill-levels of a participant, such as beginner, intermediate and advanced.

Thus, one embodiment enables the participant to receive instructions from famous people associated with the activity while contemporaneously performing the activity. Furthermore, these instructions may come in the form of the vernacular associated with the activity, thus making the instructions more enjoyable to listen to and ultimately more relevant to the participant.

Figure 5:
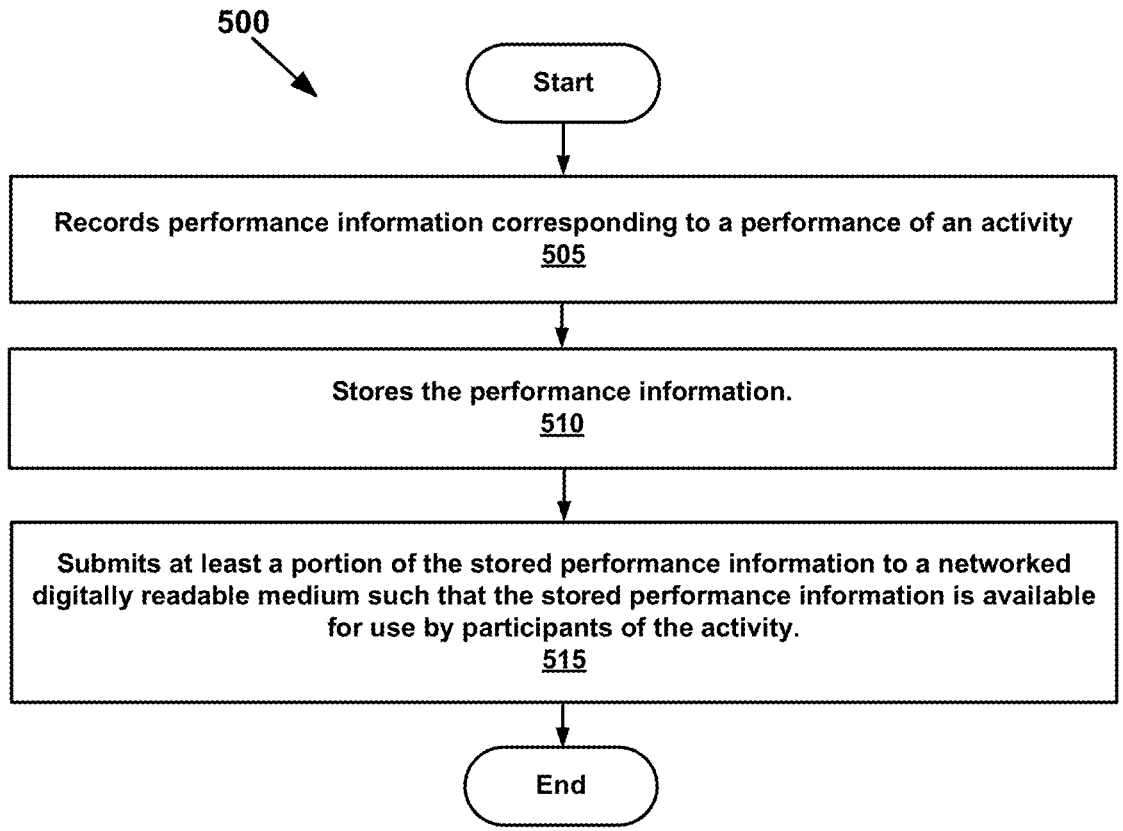
FIG. 5 is a flowchart of an example method for participating in an activity, in accordance with an embodiment.

Referring now to 500 of FIG. 5, a method for virtually competing is shown. Referring now to 505 of FIG. 5, performance information corresponding to a performance of an activity is recorded. In one embodiment, different performances of the activity are recorded. The same participant or a combination of different participants may record performance information. In one embodiment, this performance information is recorded on system 100.

Referring now to 510 of FIG. 5, in one embodiment, the performance information is stored to a memory. In one embodiment, the memory resides on system 100. In another embodiment, and referring to 515 of FIG. 5, at least a portion of the stored performance information of 510 is submitted to a networked digitally readable medium such that the stored performance information is available for use by participants of the activity.

In one embodiment and as described herein, the digitally readable medium generates a rating for the performance of the activity compared to other submitted performances of the activity. In yet another embodiment and as described herein, the networked digitally readable medium determines a winner of the submitted performances of the activity. In one embodiment and as described herein, the networked digitally readable medium provides recommendations regarding appropriate component selection for improved performance of the activity. In yet another embodiment and as described herein, the networked digitally readable medium stores performance information corresponding to, but not limited to, one or more of the following: shock absorption; cadence; velocity; gear positioning; suspension; participant's heart rate; power; time; breaking; cornering speed; and calories burned.

Thus, one embodiment enables multiple performances of the same activity to be compared against each other. Further, one embodiment enables a method for enhancing revenue generation by recommending appropriate component selection to improve a participant's performance. Moreover, one embodiment enables a method for virtually competing is an activity.

Example Computer System Environment

Figure 8:
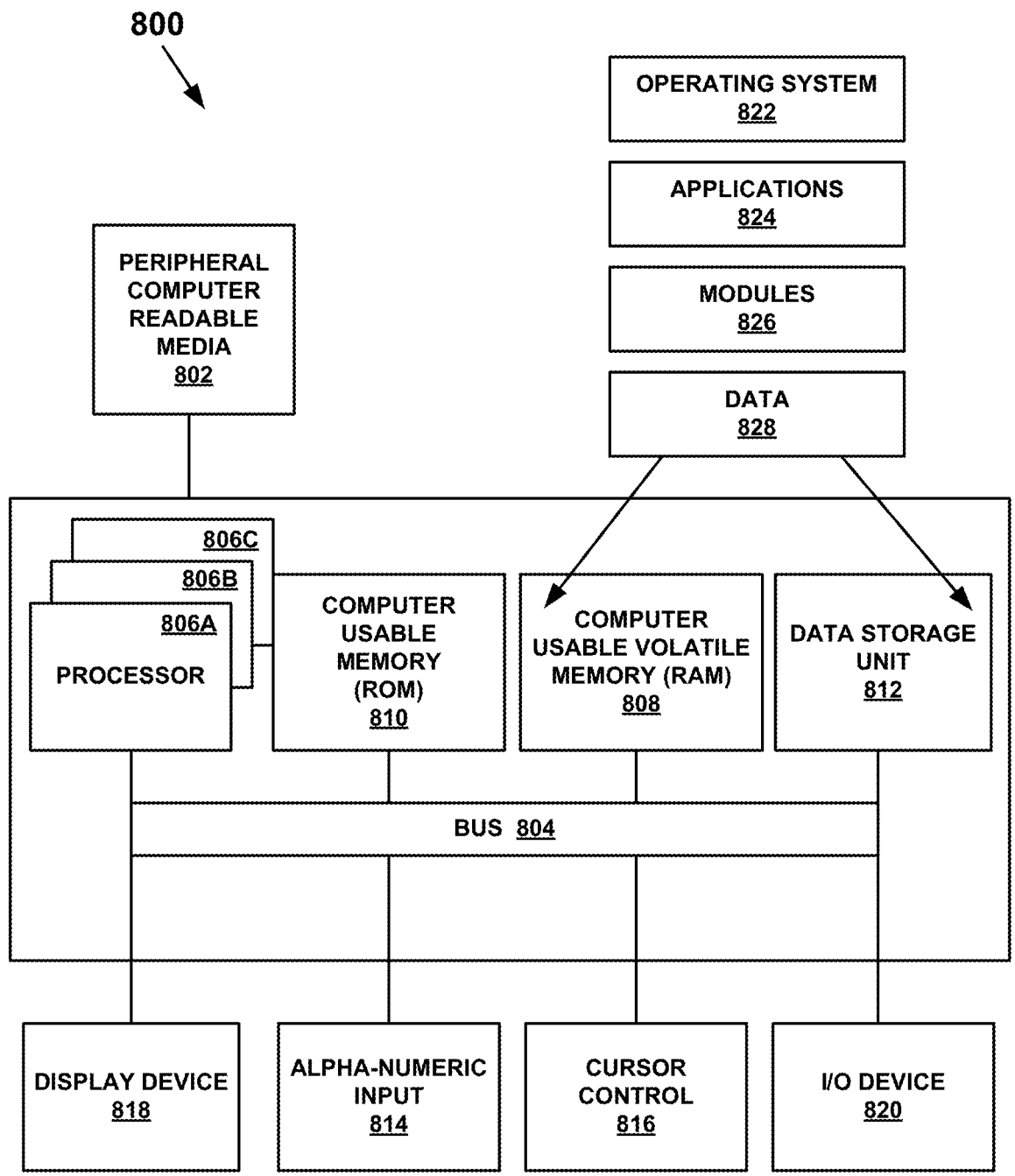
FIG. 8 is a diagram of an example computer system enabling performance comparison of multiple performances of an activity, in accordance with an embodiment.

FIG. 8 illustrates an example computer system 800 used in accordance with one embodiment. It is appreciated that system 800 is an example only and that embodiments can operate on or within a number of different computer systems including, general purpose networked computer systems, embedded computer systems, routers, switches, server devices, user devices, various intermediate devices/artifacts, stand-alone computer systems, mobile devices, and the like. As shown in FIG. 8, computer system 800 is well adapted to having peripheral computer readable media 802 such as, for example, a compact disc, and the like coupled therewith.

System 800 of FIG. 8 includes an address/data bus 804 for communicating information, and a processor 806A coupled to bus 804 for processing information and instructions. As depicted in FIG. 8, system 800 is also well suited to a multi-processor environment in which a plurality of processors 806A, 806B, and 806C are present. Conversely, system 800 is also well suited to having a single processor such as, for example, processor 806A. Processors 806A, 806B, and 806C may be any of various types of microprocessors. System 800 also includes data storage features such as a computer usable volatile memory 808, e.g. random access memory (RAM), coupled to bus 804 for storing information and instructions for processors 806A, 806B, and 806C.

System 800 also includes computer usable non-volatile memory 810, e.g. read only memory (ROM), coupled to bus 804 for storing static information and instructions for processors 806A, 806B, and 806C. Also, present in system 800 is a data storage unit 812 (e.g., a magnetic or optical disk and disk drive) coupled to bus 804 for storing information and instructions. System 800 also includes an optional alpha-numeric input device 814 including alphanumeric and function keys coupled to bus 804 for communicating information and command selections to processor 806A or processors 806A, 806B, and 806C. System 800 also includes an optional cursor control device 816 coupled to bus 804 for communicating user input information and command selections to processor 806A or processors 806A, 806B, and 806C. System 800 also includes an optional display device 818 coupled to bus 804 for displaying information.

Referring still to FIG. 8, optional display device 818 of FIG. 8 may be a liquid crystal device, cathode ray tube, plasma display device or other display device suitable for creating graphic images and alpha-numeric characters recognizable to a user. Optional cursor control device 816 allows the computer user to dynamically signal the movement of a visible symbol (cursor) on a display screen of display device 818. Many implementations of cursor control device 816 are known in the art including a trackball, mouse, touch pad, joystick or special keys on alpha-numeric input device 814 capable of signaling movement of a given direction or manner of displacement. Alternatively, it will be appreciated that a cursor can be directed and/or activated via input from alpha-numeric input device 814 using special keys and key sequence commands.

System 800 is also well suited to having a cursor directed by other means such as, for example, voice commands or haptic movement. System 800 also includes an I/O device 820 for coupling system 800 with external entities.

Referring still to FIG. 8, various other components are depicted for system 800. Specifically, when present, an operating system 822, applications 824, modules 826, and data 828 are shown as typically residing in one or some combination of computer usable volatile memory 808, e.g. random access memory (RAM), and data storage unit 812. However, it is appreciated that in some embodiments, operating system 822 may be stored in other locations such as on a network or on a flash drive; and that further, operating system 822 may be accessed from a remote location via, for example, a coupling to the Internet. In one embodiment, the present invention, for example, is stored as an application 824 or module 826 in memory locations within RAM 808 and memory areas within data storage unit 812.

Computing system 800 is one example of a suitable computing environment. In one embodiment, computing system 800 is modifiable to include more, fewer, or different components based on the scope of use and/or functionality requirements of system 100.

Moreover, embodiments may be described in the general context of computer-executable instructions, such as program modules, being executed by a computer. Generally, program modules include routines, programs, objects, components, data structures, etc., that perform particular tasks or implement particular abstract data types. One embodiment can also be practiced in a distributed computing environment where tasks are performed by remote processing devices that are linked through a communications network. In a distributed computing environment, program modules may be located in both local and remote computer-storage media including memory-storage devices.

Recreating a Performance of an Activity from a Camera Perspective

In one embodiment, a performance of an activity is recreated from a camera's perspective. For example, a camera is coupled with a participant during an activity. The camera generates a video feed (or one or more images) of the performance of the activity. In one example, the activity being performed is mountain biking. While the following explanation refers to mountain bike riding, embodiments are not limited to such an activity.

In one embodiment, a location tracking device is used to map the trail traversed by the mountain biker. The actual video taken by the camera is then correlated with the altitude and map log (generated by the location tracking device) to create (via a computer, the web, or the like) a real time re-creation of a ride from the camera's perspective with enhanced effects. In one embodiment, the video camera is equipped with a location marker feed from the location tracking device and digital location data is placed in the digital video feed at the location tracking device sampling rate (e.g. user designated or by location differentiation and change rate based sampling or other suitable sampling rate).

In one embodiment, the location tracking device includes a transmitter for transmitting obtained location and altitude data; and the video camera marker feed includes a receiver for receiving the transmitted data. The marker feed further includes a data buffer, a processor and suitable video correlation software. In one embodiment, the marker feed is wired or wireless and the location tracking device data may be associated with the video along with date time data generated by the video camera. In one embodiment, the marker feed includes a real time pairing buffer in which video data temporarily resides while corresponding location tracking device is associated with corresponding "frames" or video sectors.

In one embodiment, the mountain biker carries a display screen, coupled with the camera, that shows a split screen graphic showing the altitude and map aside the rider perspective video. As described herein, training recommendations may be included on the display screen or through cues (e.g., audio, visual, haptic, and the like).

In one embodiment, the location data together with the rider perspective video ("data pack") is correlated with a map system so that the data pack may be tied to the actual location of the participant's performance. Mountain bike riders are then able to "shop" online for riding venues that they may wish to visit.

The location and map system data may also be used to augment the video data when video is missing. For example, if only segments of a ride were actually taped, intervening portions may be interpolated and graphically simulated using the map system and/or the actual location data. In this manner, a party may view a virtual composite ride of their own designation including elements of real video as well as simulated video. In one embodiment, a processor ties various pre-recorded ride segment together to form a user chosen trail map and presents the segment data in a coherent and continuous fashion as if the chosen trail data had been contiguously generated.

Figure 9:
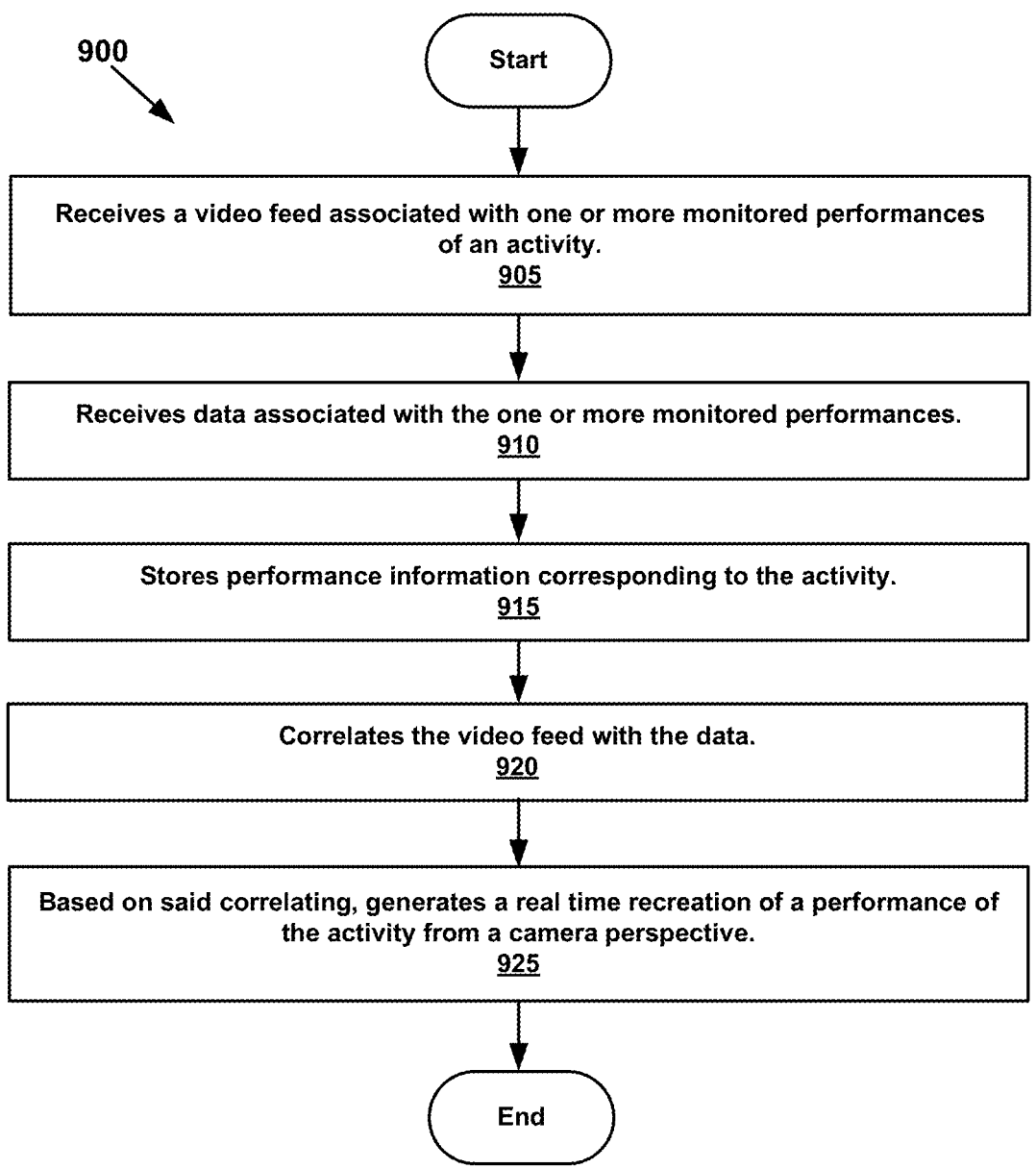
FIG. 9 is a flowchart of an example method for recreating a performance of an activity from a camera perspective, in accordance with an embodiment.

Referring now to FIG. 9, a flowchart 900 of a method for recreating a performance of an activity from a camera perspective is shown. Referring now to 905 of FIG. 9, a video feed associated with one or more monitored performances of an activity is received. The video feed may originate from any type of camera that can capture images and is capable of being coupled with a participant while performing the activity.

Referring now to 910 of FIG. 9, in one embodiment and as described herein, location and/or altitude data (performance information) associated with the one or more monitored performances is received. Referring now to 915 of FIG. 9, in one embodiment and as described herein, performance information corresponding to the activity is stored. Referring now to 920 of FIG. 9, in one embodiment, the imagery is correlated with the performance information. Referring now to 925 of FIG. 9, in one embodiment, based on the correlation, a real time recreation of the activity is generated from a camera's perspective.

In one embodiment, a rider perspective video is presented to a participant. However, in another embodiment, a split screen graphic showing an altitude and map aside the rider perspective video is presented to a participant. In one embodiment, the real time recreation of a ride from a camera perspective is correlated with a map system such that the correlated video feed and the data is linked to a real location.

In one embodiment, and as described herein comparative performance data is provided to a participant based on the received data associated with the one or more monitored performances and the stored performance information. In one embodiment, a recommendation corresponding to the improved performance of the activity is provided. In another embodiment, a recommendation for an appropriate component selection for improved performance of the activity is generated. In yet another embodiment, a recommendation for a component operation for improved performance of the activity is generated. As disclosed herein, in one example, feedback to a user is provided while the user is participating in the activity. This feedback to a user may include a voice of a person of interest to the participant. The feedback to the user may be through generated visual cues. The feedback to the user may also be through generated audio, haptic, or other cues.

In another embodiment and as described herein, the comparative performance forms a basis of a virtual race competition. In yet another embodiment and as described herein, one or more of the monitored performances is rated.

In one example and as described herein, one or more downloadable participatory activities is provided. In another example, a map system is used to augment the video feed associated with the one or more monitored performances of the activity by interpolating and graphically simulating a portion of the video feed of the activity that is missing.

In one embodiment, the image recording apparatus includes: an aperture for directing optical wavelengths; an optical to digital transducer in a path of the wavelengths; a wireless receiver having communication protocol instructions; an antenna connected to the wireless receiver; a memory having correlation instructions for correlating data received by the receiver with digital output from the optical to digital transducer; and a processor for running the correlation instructions.

Incorporating Real World Physical Activity into a Virtual World Environment

Figure 10:
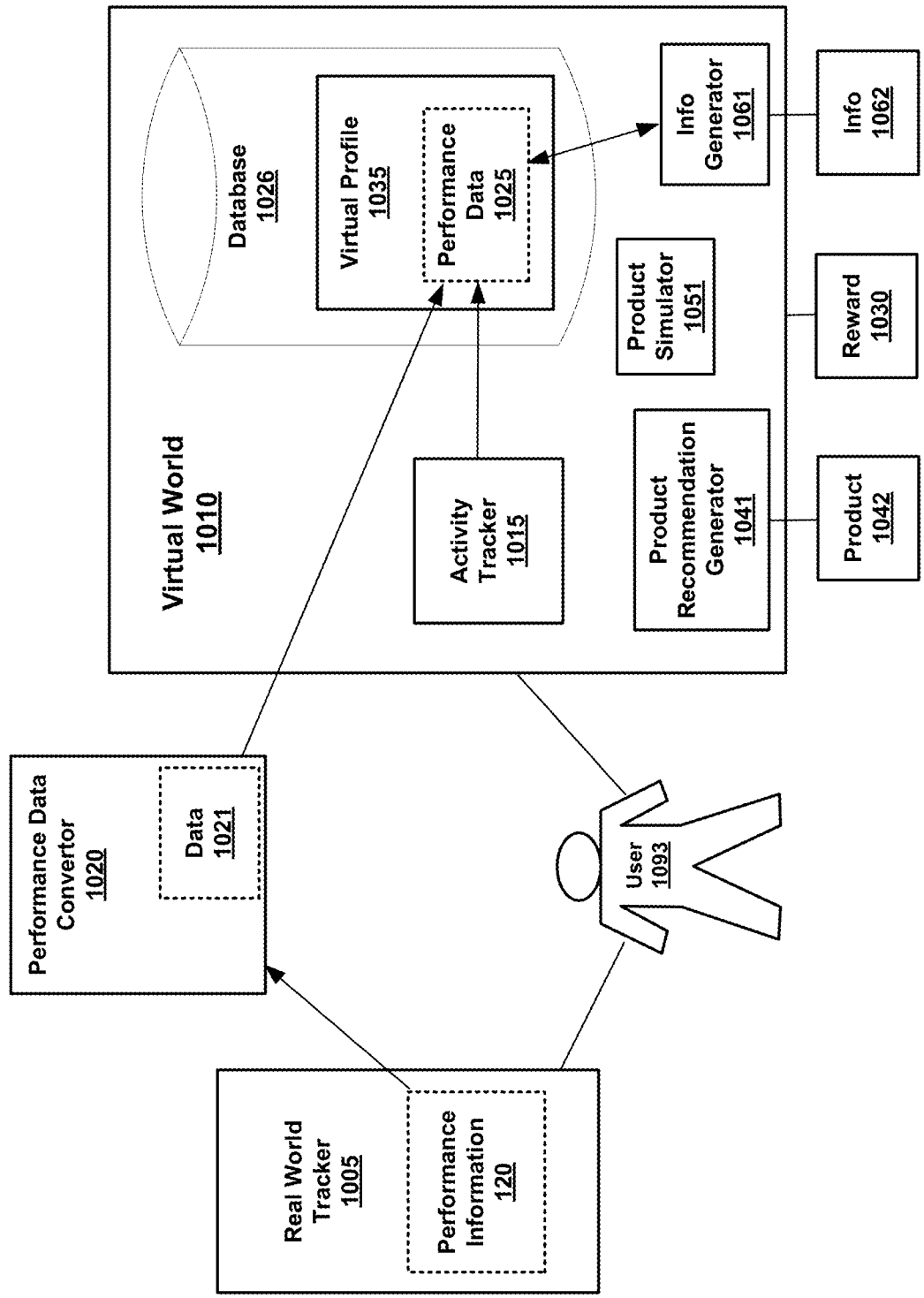
FIG. 10 is a block diagram of a system configured to convert user activities performed in a real world into virtual world activity, in accordance with an embodiment.

With reference now to FIG. 10, a block diagram of a system 1000 configured to convert user activities performed in the real world into virtual world environment activity is shown in accordance with an embodiment.

In one embodiment, system 1000 includes a virtual world environment 1010, a real world activity tracker 1005 (e.g., system 100 described and shown in FIGS. 1-9), and a real world activity to virtual world activity convertor 1020.

In one embodiment, the virtual world environment 1010 includes a virtual activity tracker 1015 that obtains virtual activity performance data 1025 for an activity performed by the user 1093 in the virtual world environment 1010. In one embodiment, virtual world environment 1010 includes a virtual world database 1026 to store the virtual activity performance data 1025 in a virtual profile 1035 of the user 1093.

In one embodiment, real world activity tracker 1005 obtains real world activity performance data (e.g., performance information 120) for a real world activity performed by the user 1093 and stores the real world activity performance data in a real world data file (e.g., activity information module 115, computer 210, etc. of FIG. 2). For purposes of clarity, the discussion of the real world activity tracker 1005 (e.g., system 100) is not repeated herein, but is included in FIGS. 1-9 and their accompanying description.

In one embodiment, real world activity to virtual world activity convertor 1020 converts the real world activity performance data (e.g., performance information 120) into an amount of converted virtual activity performance data 1025 and adds it to the virtual profile 1035 of the user 1093.

In one embodiment, the real world activity to virtual world activity convertor 1020 provides a one-to-one conversion of the real world activity performance data (e.g., performance information 120) as the amount of converted virtual activity performance data 1025.

In one embodiment, the real world activity to virtual world activity convertor 1020 provides a tiered conversion of the real world activity performance data (e.g., performance information 120) to the amount of converted virtual activity performance data 1025. In one embodiment, the tiered conversion is based on a user metric such as an initial fitness level, a goal, a virtual world setting, and the like.

In one embodiment, the addition of the amount of converted virtual activity performance data 1025 to the virtual profile 1035 of the user 1093 causes a reward 1030 to be provided to the user 1093 from virtual world environment 1010. In one embodiment, reward 1030 is a number of reward points, a virtual upgrade, an opportunity to enter/use a video game with an advantage, a discounted offer for a product, an invitation to a virtual event, an invitation to a real world event, or the like.

In one embodiment, virtual world environment 1010 includes a product recommendation generator 1041 that provides a recommendation for a real world product 1042 to the user 1093. In one embodiment, virtual world environment 1010 includes a product simulator 1051 that allows the user 1093 to virtually test the real world product 1042 recommended by the product recommendation generator 1041.

In one embodiment, virtual world environment 1010 includes an information generator 1061 that provides performance information 1062 to the user 1093. In one embodiment, the performance information 1062 is based on the virtual activity performance data 1025 in the virtual profile 1035 of the user 1093.

Figure 11:
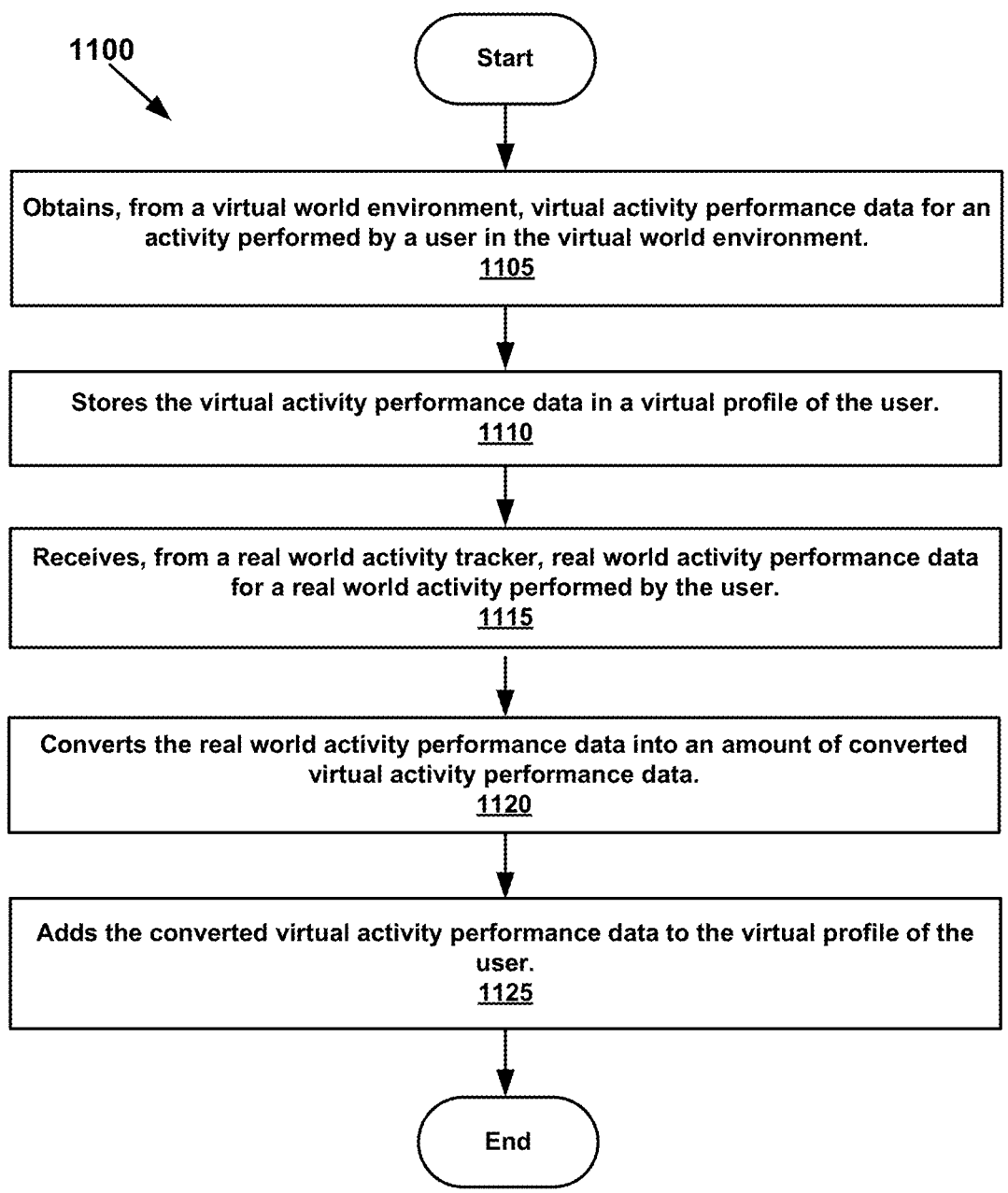
FIG. 11 is a flowchart of an example method for converting user activities performed in the real world into virtual world activity, in accordance with an embodiment.

Referring now to FIG. 11, a flowchart 1100 of an example method for converting user activities performed in the real world into virtual world activity is shown in accordance with an embodiment. Thus, in one embodiment, a user's performance in the real world will apply to virtual world environment 1010. E.g., a user's real world profile and/or achievements (e.g., performance information 120) will affect the user's game profile and/or achievements in virtual world environment 1010.

With reference now to 1105 of FIG. 11, one embodiment obtains, from virtual world environment 1010, virtual activity performance data 1025 for an activity performed by a user 1093 in the virtual world environment.

Referring now to 1110 of FIG. 11, one embodiment stores the virtual activity performance data 1025 in a virtual profile 1035 of the user 1093.

Referring now to 1115 of FIG. 11, one embodiment receives, from a real world activity tracker (e.g., system 100 of FIG. 2), real world activity performance data (e.g., performance information 120) for a real world activity performed by the user 1093. For example, one embodiment keeps track of a user's physical performance and then uses the physical performance to augment the user's position in the virtual world environment 1010. That is, different levels are awarded, better/different virtual machinery is awarded, better/different virtual parts are awarded, virtual achievements are obtained, and the like.

In one embodiment, the physical performance is a bike ride, swim, run, hike, walk, drive, motorized ride (e.g., motorcycle, snowmobile, all-terrain vehicle (ATV), utility task vehicle (UTV), side-by-side, boat, personal watercraft, etc.), or the like. In one embodiment, the virtual world environment 1010 is an app or program that runs in conjunction with a treadmill, a stationary bike, an elliptical machine, a simulator (e.g., an airplane simulator, a racecar simulator, a motorcycle simulator, an off-roading simulator, etc.), or the like.

One embodiment provides a performance evaluation (e.g., information 1062) to the user 1093, where the performance evaluation (e.g., information 1062) includes an analysis of the virtual activity performance versus the real world activity performance. In one embodiment, the performance evaluation (e.g., information 1062) will include a performance review based on the analysis. In one embodiment, the performance review will be provided to the user 1093 in the virtual world environment 1010.

Referring now to 1120 of FIG. 11, one embodiment converts the real world activity performance data (e.g., performance information 120) into an amount of converted virtual activity performance data 1021. For example, the user 1093 tracks their progress in the real world using system 100, e.g., a bike ride tracked with a location tracking device, a swim tracked with a smartwatch, a race run with a timing chip, etc. The tracked information from system 100 is then used to provide achievement in the user's virtual world environment 1010.

In one embodiment, the conversion is a one-to-one conversion of the real world activity performance data (e.g., performance information 120) as the amount of converted virtual activity performance data 1021. For example, if the actual bike ride were 100 miles, those 100 miles would be applied to the virtual world environment 1010. The application in the virtual world environment 1010 would accept the 100 miles (or a virtual correlation to a real 100 miles) as though they had been performed in the virtual world environment 1010. As such, if there is a level upgrade for the total distance covered, the 100 actual miles ridden would be awarded to the user 1093 in the virtual world environment 1010. The awarded miles will result in a better virtual bike, a higher health score, an unlocked achievement/level, etc.

Similarly, the user 1093 tracks their workout time in the real world. For example, a bike ride that took 2 hours. Those 2 hours would be applied to the virtual world environment 1010. The virtual world environment 1010 would accept the 2 hours of performance from system 100 and add them to the user's profile in the virtual world environment 1010. As such, if there is a level upgrade (or the like) for the total time ridden, the 2 hours (or some virtual relation) would be awarded to the user 1093. The award of the 2 hours would result in a better virtual bike, a higher health score, an advancement to a higher level, etc. Although bike riding is used in the example, the physical act of swimming, running, hiking, walking, driving, and the like, are similarly incorporated into the virtual world environment 1010.

In one embodiment, the conversion is a tiered conversion of the real world activity performance data (e.g., performance information 120) as the amount of converted virtual activity performance data 1021, where the tiered conversion based on a user metric such as, but not limited to, an initial fitness level, a goal, a virtual world environment 1010 setting, and the like. For example, instead of providing a one-to-one correlation, the virtual game provides a mark-up in the value of the actual physical task. For example, each actual single mile ridden (or run, swum, driven, etc.) would result in 2 (or any defined value) virtual miles being added to the user's virtual world environment 1010 avatar.

In one embodiment, the correlation is dependent upon the task performed in the real world. For example, a 5 mile walk around a neighborhood provides a one-to-one five miles to the user's virtual world environment 1010 performance, while a 5 mile hike up a hill (identified by a tracked route on a map, or elevation change) would result in a two-to-one correlation, e.g., 10 miles in the virtual world environment 1010, or a double on the health of the virtual avatar, etc.

In another example, a 100 mile drive on the freeway may result in a one-to-five (or whatever defined ratio) reduced correlated value for a user's off-road virtual world environment 1010. While a weekend of off-roading that resulted in 100 miles driven on trails would be credited at an increased value (e.g., a five-to-one ratio) in the user's off-road virtual world environment 1010.

In one embodiment, the correlated value is a tiered value that will change depending upon the time or distance covered for an overall activity. For example, hikes along level terrain are correlated as two-to-one for the first 100 miles (or 20 hours), then drops down to a one-to-one correlation for the next 400 miles, and further drop down to a less than one-to-one correlation for any miles over 500. In so doing, the virtual world environment 1010 would provide an incentive for a user 1093 to move on to a bigger challenge (e.g., a hike with elevation change), or a different challenge (e.g., running, guided activities (e.g., a hike along a suggested trail), or the like), in the real world.

Although a number of correlations are discussed, it should be appreciated that the correlations are adjustable, and can be adjusted dependent upon a user's initial fitness level, a user's goals, a user's virtual world settings, or the like.

For example, if a user 1093 was using a virtual running simulator on a treadmill and had a goal of running a 10 k, the virtual running simulator notes that the user 1093 is presently able to run a 12-minute mile pace for 1 kilometer, slows down to a walk for the second kilometer, and repeats the run/walk alternation for the entire 10 k. Moreover, the virtual running simulator has a number of different runs available and provide the user 1093 with access to new running path as achievements as the user 1093 advances in distance, time, pace, etc. The virtual running simulator will inform the user 1093 that a neighborhood run (e.g., tracked with a user's smart device and corroborated by system 100) will result in a given number of reward points, the opening of a new run path simulation, the unlocking or an achievement, or the like. As such, the virtual world environment 1010 would prompt the user 1093 to take a run in the real world (e.g., outside and not on the treadmill, elliptical, or the like) and then reward the user 1093 accordingly.

In one embodiment, the virtual world environment 1010 also provides recommendations regarding appropriate component selection for improved performance of the real world activity. For example, the product recommendation generator 1041 will provide a recommendation for a real world product 1042 that would be appropriate for the user 1093. In other words, the virtual world environment 1010 will provide real world recommendations, information, coaching, guidance, or the like that would be of value to the user 1093. For example, a shoe recommendation based on a user's physical level, body type, weight, build, gender, etc.

Moreover, in one embodiment, the virtual world environment 1010 provides end-of-life information or upgrade information (such as about the user's shoes). For example, after the user 1093 runs 200 kilometers, the virtual world environment 1010 informs the user 1093 that the currently used shoes are approaching an end-of-life and should be replaced. In one embodiment, the virtual world environment 1010 will provide a new shoe recommendation based on the user's post 200 kilometer fitness level, weight changes, health, etc.

In another example, if a user 1093 was using a virtual bike simulator on an indoor bike (stationary bike, bike on an indoor bike stand, or the like) and had a goal of riding in a fire road race (gravel grinder, or the like), the virtual bike simulator notes that the user 1093 is presently able to ride a road bike at a good pace. Moreover, the virtual bike simulator has a number of different fire road video simulations available and provides the user 1093 with access to new fire road video simulations as the user 1093 advances in distance, time, pace, etc. The virtual bike simulator will inform the user 1093 that a fire road ride tracked with a user's smart device (and in one embodiment, verified by system 100) will result in an additional number of reward points, the opening of a new fire road video simulations, a change to enter/use an advantage, or the like. As such, the virtual world environment 1010 would provide enticement for the user 1093 to take a ride in the real world.

In one embodiment, the virtual world environment 1010 also provides real world bike (or bike component) information that would be of value to the user 1093. For example, an initial bike recommendation (or bike component upgrade recommendation) based on a user's physical level, body type, weight, build, gender, present bicycle, performance goals, etc. Moreover, the virtual world environment 1010 provides upgrade information specific to the user's bike, performance level, etc. For example, after the user 1093 rides 1000 kilometers, the virtual world environment 1010 would inform the user 1093 of the best upgrade(s) for the user's bike that would result in realized performance increases, and further make the recommendations based on the user's post 1000 kilometer fitness level, weight changes, etc.

In one embodiment, the virtual bike provided by the virtual bike simulator is based on the user's present bicycle and present bicycle set-up. As the user 1093 progresses, the virtual bike simulator will suggest a component change, setting change, new component, etc. (e.g., a new rear shock, setting change for an existing shock, geometric set-up adjustment, or the like) for the user's real-world bike. In one embodiment, the suggestion will include an image or video of the suggested component, installation, configuration change, and the like.

In one embodiment, the component selection is added to a simulation in the virtual world environment 1010. The virtual world environment 1010 will obtain virtual activity performance data 1025 for a virtual activity performed by the user 1093 with the simulated components in the virtual world environment 1010. In one embodiment, an evaluation of the virtual activity performance data 1025 using the simulated components will be presented to the user 1093. For example, the virtual bike product simulator 1051 is able to provide the user 1093 with a ride in the virtual world environment 1010 on the user's existing bike set-up and then provide the user 1093 with the same virtual world environment 1010 ride after the user's bike has been virtually upgraded with the suggested component or product 1042 (for example, a change in the resistance to emulate a sprocket upgrade, a change in ride angle to emulate a geometry change, etc.).

In so doing, the user 1093 would be able to virtually test different components, products, and configurations on their existing bicycle to determine which would provide an increase in speed for the same pedal pressure, which would provide the smoothest ride across the terrain (e.g., allow the user 1093 to obtain a higher speed across the terrain without losing grip, without crashing, etc.) Thus, the virtual world environment 1010 would provide product simulator 1051 capabilities that would enable the user 1093 to pre-test upgrades or changes to the user's real world bicycle virtually. Moreover, after performing a real world upgrade, the user 1093 would be able to record a physical ride (such as by using system 100) and then upload it to the virtual world environment 1010. In so doing, the user 1093 would be able to obtain feedback (e.g., information 1062) in the virtual world environment 1010 about her bike's pre- and post-upgrade performance in the real world.

In one embodiment, the user 1093 rides (or performs another activity) on the real world version of the virtual world environment 1010. For example, the virtual world environment 1010 simulation is of fire road Charlie 120 k. The user 1093 would ride the physical world fire road Charlie 120 k and record the ride such as via system 100. The physical world ride information is then collected by real world activity tracker 1005 and provided via performance data convertor 1020 to the virtual world environment 1010. Based on the information provided, the user 1093 is rewarded with reward 1030 which could be virtual world points, one or more new virtual rides, or the like.

Further, in one embodiment, the virtual world environment 1010 will use the metrics from the user's physical ride as a "ghost" or "avatar" within the virtual world environment 1010 when the user 1093 is virtually riding "fire road Charlie 120 k." In so doing, the user 1093 would be able to use the virtual world environment 1010 to compare their present riding with their previous fire road Charlie 120 k ride using information generator 1061. The comparison will find points of weakness in their ride, points of strength in their ride, perform an evaluation of their training regime, and identify one or more changes that they should make (e.g., are up-hills a bit weak, down-hills a bit slow, better times/locations to take in calories, water, or other nutrients, etc.). For example, the information generator 1061 compares the performance of the user 1093 over time (or different real world rides) to determine whether that specific user would be better off fueling up at the 40 k mark before a big hill climb or at the 50 k mark at a flat portion of the ride and after the completion of the big hill climb.

Referring now to 1125 of FIG. 11, one embodiment adds the converted virtual activity performance data 1021 to the virtual profile 1035 of the user 1093. In one embodiment, a reward 1030 is provided to the user 1093 when the amount of converted virtual activity performance data 1021 is added to the virtual profile 1035 of the user 1093. In one embodiment, the reward 1030 is one or more of a number of reward points, a virtual upgrade, an opportunity to enter/use a video game with an advantage, a discounted offer for a product, an invitation to a virtual event, an invitation to a real world event, or the like.

In one embodiment, information generator 1061 of the virtual world environment 1010 provides information 1062 such as an event invitation, enticement, encouragement, and/or advancement in one or both of the virtual world environment 1010 and the real world. For example, when using a virtual world driving simulator, information generator 1061 suggests that the user 1093 drive in a track day at the local racetrack, invites the user 1093 to enter a virtual race, offers the user 1093 an opportunity to drive in a track day, and the like.

In one embodiment, the user 1093 accepts the offer and (for example) drives in a track day. The physical world performance information 120 is then provided to the virtual world environment 1010 driving simulator and information generator 1061 is used to analyze the user's real world performance. The analysis will provide information 1062 that can include areas of developmental needs, areas of good performance, and the like.

In one embodiment, information 1062 is provided to the user 1093 and the user selects (or the virtual world driving simulator would automatically select) one or more of these areas to review, complement, provide instruction, provide homework assignments, and the like.

The user 1093 again works in the virtual driving world simulator and after a given time period (or apparent performance increase) the information 1062 will suggest the user 1093 drive in another track day. At the next real world track day, the user's real world performance information 120 is provided via performance data converter 1020 to the virtual world environment 1010 driving simulator. The new track day information is used by information generator 1061 to compare and contrast the user's real world performances. This resulting information 1062 would be valuable and provide insight as to where the user 1093 has increased their capability. Such feedback would also provide real world confidence to the user 1093 and show the user the value of the virtual world environment 1010 driving simulator.

In one embodiment, the virtual world environment 1010 driving simulator would also reward the user 1093 based on the physical world track day performance. The reward 1030 can be a new level, an achievement upgrade, a new racetrack view, or the like. In one embodiment, as in the bike example above, the virtual world environment 1010 product recommendation generator 1041 will suggest one or more different product(s) 1042 that would further enhance the user's real world vehicle performance. The product(s) 1042 include suspension components, tires, upgrades, tunes, or the like. In one embodiment, the virtual world environment 1010 also provides a coupon, discount, advantage, or other reward 1030 along with the suggested one or more different product(s) 1042.

In one embodiment, the coupon, discount, or other reward 1030 is based on the real world performance. For example, if the user 1093 makes a real world lap time of under 2 minutes, the virtual world environment 1010 driving simulator would provide a coupon for 5% off, but if the user 1093 makes a real world lap time of under 1 minute 45 seconds, the virtual world environment 1010 driving simulator would provide a coupon for 10% off. In one embodiment, the coupon, discount, or other reward 1030 is based on the user's real world lap time as compared to the user's virtual world lap time.

In one embodiment, the virtual world environment 1010 is used to compete with another virtual world user, a plurality of virtual world users, or the like. For example, using the fire road Charlie 120 k, the virtual world environment(s) will build a virtual fire road Charlie 120 k event. The event includes prizes, rewards, bonuses, and the like. Moreover, since it is a virtual event, the event is a user's virtual ride of the 120 k on a given day at a given time. For example, the virtual riders are all shown at a starting line and then are shown as avatars or the like during the virtual race so that a virtual user 1093 will feel like they are part of an actual competition.

In another embodiment, if the user 1093 is not a competitive person or would rather ride the race alone, the virtual event is based on the user's best virtual ride of the 120 k over a given time period (e.g., a day, week, month, year, etc.), or the like.

In one embodiment, the event is a combination of the user's virtual ride of the fire road Charlie 120 k and a user's real world 120 k ride (such as a ride tracked by system 100). In one embodiment, the real world 120 k ride is handicapped based on elevation changes (or lack thereof), type of terrain ridden, average ride elevation, and the like. In so doing, the real world ride can be fairly compared over different real world courses ridden by different riders.

In one embodiment, a virtual event is broken down into smaller events. For example, a 100 k virtual event is broken down into one or more of a 10 k ride, 20 k ride, 50 k ride, etc., such that users of different capabilities would be able to compete in the virtual event. For example, users of different fitness levels can complete a 100 k event by completing 2-50 k rides, 4-25 k rides, 10-10 k rides, or the like.

Moreover, in one embodiment, the user's race selection and category would be decided by the virtual world environment 1010. E.g., such that a professional level bike rider would not be allowed to compete in the 20 k amateur race, etc. In one embodiment, the virtual race is promoted by real brands. For example, sponsors for the virtual event can include FOX racing, energy foods/drinks, other advertisers, etc.

The foregoing Description of Embodiments is not intended to be exhaustive or to limit the embodiments to the precise form described. Instead, example embodiments in this Description of Embodiments have been presented in order to enable persons of skill in the art to make and use embodiments of the described subject matter. Moreover, various embodiments have been described in various combinations. However, any two or more embodiments could be combined. Although some embodiments have been described in a language specific to structural features and/or methodological acts, it is to be understood that the subject matter defined in the appended claims is not necessarily limited to the specific features or acts described above. Rather, the specific features and acts described above are disclosed by way of illustration and as example forms of implementing the claims and their equivalents.

What is claimed is:

1. A system comprising:
a virtual world environment comprising:
a virtual activity tracker configured to obtain virtual activity performance data for an activity performed by a user in said virtual world environment; and
a virtual world database configured to store said virtual activity performance data in a virtual profile of said user;
a real world activity tracker configured to obtain real world activity performance data for a real world activity performed by said user and store said real world activity performance data in a real world data file, wherein said real world activity performance data is obtained as said user transports said real world activity tracker, said real world activity tracker providing said real world activity performance data to a product recommendation generator; and
a real world activity to virtual world activity convertor configured to
convert said real world activity performance data into an amount of converted virtual activity performance data; and
add said converted virtual activity performance data to said virtual profile of said user, wherein said virtual world environment further comprises:
said product recommendation generator configured to provide a recommendation for a real world product to said user, and
a product simulator configured to allow said user to virtually test said real world product recommended by said product recommendation generator.

2. The system of claim 1, wherein said real world activity to virtual world activity convertor is configured to provide a one-to-one conversion of said real world activity performance data as said amount of converted virtual activity performance data.

3. The system of claim 1, wherein said real world activity to virtual world activity convertor is configured to provide a tiered conversion of said real world activity performance data to said amount of converted virtual activity performance data.

4. The system of claim 3, wherein said tiered conversion is based on a metric of said user, said metric selected from the group consisting of: an initial fitness level, a goal, and a virtual world setting.

5. The system of claim 1, wherein said addition of said amount of converted virtual activity performance data to said virtual profile of said user is configured to cause a reward to be provided to said user.

6. The system of claim 5, wherein said reward is selected from the group consisting of: a number of reward points, a virtual upgrade, an opportunity to enter/use a video game with an advantage, a discounted offer for a product, an invitation to a virtual event, and an invitation to a real world event.

7. The system of claim 1, wherein said virtual world environment further comprises:
an information generator configured to provide performance information to said user, said performance information based on said virtual activity performance data in said virtual profile of said user.

8. A non-transitory computer usable storage medium comprising instructions that when executed by at least one processor of a computer, cause said at least one processor to perform a method for converting real world activity into virtual world activity, said method comprising:
obtaining, from a virtual world environment, virtual activity performance data for an activity performed by a user in said virtual world environment;
storing said virtual activity performance data in a virtual profile of said user;
receiving, from a real world activity tracker, real world activity performance data for a real world activity performed by said user, wherein said real world activity performance data is obtained as said user transports said real world activity tracker, said real world activity tracker providing said real world activity performance data to a product recommendation generator;
converting said real world activity performance data into an amount of converted virtual activity performance data; and
adding said converted virtual activity performance data to said virtual profile of said user and said product recommendation generator providing recommendations regarding a real world product for use by said user wherein said real world product is a component selection for improved performance of said real world activity.

9. The non-transitory computer usable storage medium of claim 8, wherein said method further comprises:
adding said component selection to a simulation in said virtual world environment;
obtaining virtual activity performance data for another activity performed by said user with said simulation in said virtual world environment; and
providing an evaluation of said virtual activity performance data to said user.

10. The non-transitory computer usable storage medium of claim 9, wherein said method further comprises:
providing a performance evaluation to said user, said performance evaluation comprising:
an analysis of said virtual activity performance versus said real world activity performance; and
a performance review based on said analysis and provided to said user in said virtual world environment.

11. The non-transitory computer usable storage medium of claim 9, wherein said method further comprises:
providing a one-to-one conversion of said real world activity performance data as said amount of converted virtual activity performance data.

12. The non-transitory computer usable storage medium of claim 9, wherein said method further comprises:
providing a tiered conversion of said real world activity performance data as said amount of converted virtual activity performance data,
said tiered conversion based on a metric of said user selected from the group consisting of: an initial fitness level, a goal, and a virtual world setting.

13. The non-transitory computer usable storage medium of claim 9, wherein said method further comprises:

providing a reward to said user when said amount of converted virtual activity performance data is added to said virtual profile of said user, said reward selected from the group consisting of: a number of reward points, a virtual upgrade, an opportunity to enter/use a video game with an advantage, a discounted offer for a product, an invitation to a virtual event, and an invitation to a real world event.

14. A system to convert real world activity into virtual world activity, said system comprising:

a virtual world environment comprising:
- a virtual activity tracker configured to obtain virtual activity performance data for an activity performed by a user in said virtual world environment;
- a virtual world database configured to store said virtual activity performance data in a virtual profile of said user;
- a product recommendation generator configured to provide a recommendation for a real world product to said user; and
- a product simulator configured to allow said user to virtually test said real world product recommended by said product recommendation generator;

a real world activity tracker configured to obtain real world activity performance data for said real world activity performed by said user and store said real world activity performance data in a real world data file, wherein said real world activity performance data is obtained as said user transports said real world activity tracker, said real world activity tracker providing said real world activity performance data to said product recommendation generator;

a real world activity to virtual world activity convertor configured to:
- receive, from said real world activity tracker, said real world data file with said real world activity performance data;
- convert said real world activity performance data into an amount of converted virtual activity performance data; and
- add said converted virtual activity performance data to said virtual profile of said user; and a performance evaluator, said performance evaluator configured to compare said virtual activity performance data with said real world activity performance data and provide a performance review, based on said comparison, to said user in said virtual world environment.

15. The system of claim 14, wherein said real world activity to virtual world activity convertor is configured to provide a tiered conversion of said real world activity performance data to said amount of converted virtual activity performance data, said tiered conversion based on a user metric selected from the group consisting of: an initial fitness level, a goal, and a virtual world setting.

16. The system of claim 14, wherein said real world activity to virtual world activity convertor is configured to provide a one-to-one conversion of said real world activity performance data as said amount of converted virtual activity performance data.

17. The system of claim 14, wherein said real world activity to virtual world activity convertor is configured to provide a reward to said user when said amount of converted virtual activity performance data is added to said virtual profile of said user, said reward selected from the group consisting of: a number of reward points, a virtual upgrade, an opportunity to enter/use a video game with an advantage, a discounted offer for a product, an invitation to a virtual event, and an invitation to a real world event.

* * * * *